US011712256B2

(12) United States Patent
Vale et al.

(10) Patent No.: US 11,712,256 B2
(45) Date of Patent: Aug. 1, 2023

(54) CLOT RETRIEVAL DEVICE FOR REMOVING OCCLUSIVE CLOT FROM A BLOOD VESSEL

(71) Applicant: NEURAVI LIMITED, Galway (IE)

(72) Inventors: David Vale, County Galway (IE); Brendan Casey, Galway (IE); Michael Gilvarry, County Galway (IE); Jacqueline O'Gorman, County Clare (IE); Kevin McArdle, County Galway (IE)

(73) Assignee: NEURAVI LIMITED, Galway (IE)

( * ) Notice: Subject to any disclaimer, the term of this patent is extended or adjusted under 35 U.S.C. 154(b) by 717 days.

(21) Appl. No.: 16/446,749

(22) Filed: Jun. 20, 2019

(65) Prior Publication Data

US 2019/0298397 A1 Oct. 3, 2019

Related U.S. Application Data

(63) Continuation of application No. 14/952,202, filed on Nov. 25, 2015, now Pat. No. 10,363,054.

(Continued)

(51) Int. Cl.
*A61B 17/221* (2006.01)
*A61F 2/01* (2006.01)
(Continued)

(52) U.S. Cl.
CPC .... *A61B 17/221* (2013.01); *A61B 17/320725* (2013.01); *A61F 2/013* (2013.01);
(Continued)

(58) Field of Classification Search
CPC .......... A61B 17/221; A61B 2017/2215; A61B 2017/2217; A61B 2017/2212; A61F 2/013
See application file for complete search history.

(56) References Cited

U.S. PATENT DOCUMENTS

| 2,828,147 A | 3/1958 | Peiffer |
| 3,361,460 A | 1/1968 | Gerhart |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins (withdrawn)

(Continued)

*Primary Examiner* — Dianne Dornbusch
(74) *Attorney, Agent, or Firm* — Troutman Pepper Hamilton Sanders LLP

(57) ABSTRACT

A clot retrieval device for removing an occlusive clot from a blood vessel. The device includes a clot engagement section having a constrained delivery configuration and an expanded deployed configuration, wherein in the expanded deployed configuration. The clot engagement section can include a plurality of peak sections configured to vary contact pressure between the clot and the device along a length of the device; and a plurality of troughs between respective peak sections comprising a clot reception space. Each peak is configured to exert a relatively high compressive force on the clot whereas each trough is configured to exert little or no compressive force on the clot.

20 Claims, 28 Drawing Sheets

Related U.S. Application Data

(60) Provisional application No. 62/084,960, filed on Nov. 26, 2014.

(51) Int. Cl.
*A61B 17/3207* (2006.01)
*A61B 17/22* (2006.01)

(52) U.S. Cl.
CPC .............. *A61B 2017/2215* (2013.01); *A61B 2017/2217* (2013.01); *A61B 2017/22034* (2013.01); *A61F 2002/016* (2013.01); *A61F 2230/008* (2013.01); *A61F 2230/0091* (2013.01)

(56) References Cited

U.S. PATENT DOCUMENTS

| | | |
|---|---|---|
| 4,455,717 A | 6/1984 | Gray |
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | Weldon et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summer et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,686 A | 7/1998 | Sato et al. |
| 5,779,716 A | 7/1998 | Cano |
| 5,800,519 A | 9/1998 | Sandock |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,221,096 B1 | 4/2001 | Aiba et al. |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz |
| 6,355,057 B1 | 3/2002 | DeMarais et al. |
| 6,361,545 B1 | 3/2002 | Macoviak |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Michael |
| 6,488,701 B1 | 12/2002 | Nolting et al. |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |

(56) References Cited

U.S. PATENT DOCUMENTS

| | | |
|---|---|---|
| 6,592,616 B1 | 7/2003 | Stack |
| 6,598,265 B2 | 7/2003 | Lee |
| 6,602,265 B2 | 8/2003 | Dubrul et al. |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,695,858 B1 | 2/2004 | Dubrul et al. |
| 6,702,782 B2 | 3/2004 | Miller |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,052,500 B2 | 5/2006 | Bashiri et al. |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Malaei |
| 7,179,273 B1 | 2/2007 | Palmer et al. |
| 7,185,922 B2 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | Depalma et al. |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin, Jr. et al. |
| 7,604,650 B2 | 10/2009 | Bergheim |
| 7,609,649 B1 | 10/2009 | Bhandari et al. |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 3,002,822 A1 | 8/2011 | Glocker et al. |
| 7,998,165 B2 | 8/2011 | Huffmaster |
| 3,021,379 A1 | 9/2011 | Thompson et al. |
| 3,021,380 A1 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |

(56) References Cited

U.S. PATENT DOCUMENTS

| | | |
|---|---|---|
| 8,357,893 B2 | 1/2013 | Xu |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 * | 4/2014 | Janardhan ............ A61B 17/221 606/200 |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,517,340 B2 | 12/2022 | Casey |
| 2001/0001315 A1 | 5/2001 | Bates |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |

(56) References Cited

U.S. PATENT DOCUMENTS

| | | |
|---|---|---|
| 2001/0051810 A1 | 12/2001 | Dubrul |
| 2002/0004667 A1 | 1/2002 | Adams et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0128680 A1 | 9/2002 | Pavolvic |
| 2002/0138094 A1 | 9/2002 | Borillo |
| 2002/0143349 A1 | 10/2002 | Ill et al. |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest |
| 2003/0004540 A1 | 1/2003 | Linder et al. |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Hyodoh et al. |
| 2003/0050663 A1 | 3/2003 | Khachin |
| 2003/0064151 A1 | 4/2003 | Klinedinst |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung |
| 2004/0153117 A1 | 8/2004 | Clubb et al. |
| 2004/0153118 A1 | 8/2004 | Clubb |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0215942 A1 | 9/2005 | Abrahamson et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020285 A1* | 1/2006 | Niermann ............ A61F 2/01 606/200 |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0233175 A1 | 10/2007 | Zaver et al. |
| 2007/0244505 A1 | 10/2007 | Gilson et al. |
| 2007/0270902 A1 | 11/2007 | Slazas et al. |

(56) References Cited

U.S. PATENT DOCUMENTS

| | | |
|---|---|---|
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0125798 A1* | 5/2008 | Osborne ............ A61B 17/221 |
| | | 606/159 |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck et al. |
| 2008/0228209 A1 | 9/2008 | Demello et al. |
| 2008/0234706 A1 | 9/2008 | Sepetka |
| 2008/0243170 A1 | 10/2008 | Jenson et al. |
| 2008/0255596 A1 | 10/2008 | Jenson |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko et al. |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0054504 A1 | 5/2011 | Wolf et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1* | 9/2011 | Aboytes ............ A61M 29/02 |
| | | 606/194 |
| 2011/0224707 A1 | 9/2011 | Miloslavski et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | Dipalma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Brandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1* | 1/2013 | Marks ............... A61B 17/221 |
| | | 606/200 |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |

(56) References Cited

U.S. PATENT DOCUMENTS

| | | |
|---|---|---|
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1* | 10/2014 | Dacuycuy ............... A61L 31/18 606/159 |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 9/2016 | Brady et al. |
| 2016/0303381 A1 | 10/2016 | Pierce et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |

(56) References Cited

U.S. PATENT DOCUMENTS

| | | |
|---|---|---|
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0007757 A1 | 1/2021 | Casey et al. |
| 2021/0228223 A1 | 7/2021 | Casey et al. |

FOREIGN PATENT DOCUMENTS

| | | |
|---|---|---|
| CN | 102307613 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 4/2010 |
| DE | 102009056450 | 6/2011 |
| DE | 102010010849 | 9/2011 |
| DE | 102010014778 A1 | 10/2011 |
| DE | 102010024085 | 12/2011 |
| DE | 102011014586 B3 | 9/2012 |
| EP | 1153581 A1 | 11/2001 |
| EP | 2301450 B1 | 11/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| GB | 2427554 A | 1/2007 |
| GB | 2494820 A | 3/2013 |
| JP | 0919438 | 1/1997 |
| JP | 2014511223 A | 5/2014 |
| JP | 2014525796 A | 10/2014 |
| JP | 2015-505250 A | 2/2015 |
| JP | 2016-513505 A | 5/2016 |
| JP | 2019-526365 A | 9/2019 |
| WO | 94/24926 | 11/1994 |
| WO | 97/27808 | 8/1997 |
| WO | 97/38631 | 10/1997 |
| WO | 99/20335 | 4/1999 |
| WO | 99/60933 | 12/1999 |
| WO | 99/56801 | 4/2000 |
| WO | 01/21077 | 3/2001 |
| WO | 02/02162 | 1/2002 |
| WO | 02/11627 | 2/2002 |
| WO | 02/43616 | 6/2002 |
| WO | 02/070061 | 9/2002 |
| WO | 02/094111 | 11/2002 |
| WO | 03/002006 | 1/2003 |
| WO | 03/030751 | 4/2003 |
| WO | 03/051448 | 6/2003 |
| WO | 2004/028571 A2 | 4/2004 |
| WO | 2004/056275 A1 | 7/2004 |
| WO | 2005/000130 A1 | 1/2005 |
| WO | 2005/027779 A2 | 3/2005 |
| WO | 2006/021407 | 3/2006 |
| WO | 2006/031410 | 3/2006 |
| WO | 2006/107641 | 10/2006 |
| WO | 2006/135823 A2 | 12/2006 |
| WO | 2007/054307 | 5/2007 |
| WO | 2007/068424 | 6/2007 |
| WO | 2008/034615 | 3/2008 |
| WO | 2008/051431 A1 | 5/2008 |
| WO | 2008/131116 | 10/2008 |
| WO | 2008135823 A1 | 11/2008 |
| WO | 2009/031338 A1 | 3/2009 |
| WO | 2009/076482 | 6/2009 |
| WO | 2009/086482 | 7/2009 |
| WO | 2009/105710 A1 | 8/2009 |
| WO | 2010/010545 | 1/2010 |
| WO | 2010/046897 A1 | 4/2010 |
| WO | 2010/075565 A2 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2011135556 A1 | 11/2011 |
| WO | 2012/052982 A1 | 4/2012 |
| WO | 2012/064726 A1 | 5/2012 |
| WO | 2012/081020 A1 | 6/2012 |
| WO | 2012/120490 A2 | 9/2012 |
| WO | 2012/110619 A9 | 10/2012 |
| WO | 2012/156924 | 11/2012 |
| WO | 2013/016435 A1 | 1/2013 |
| WO | 2013/072777 A2 | 5/2013 |
| WO | WO-2013071173 A1 * | 5/2013 ........... A61B 17/221 |
| WO | 2013/105099 A2 | 7/2013 |
| WO | 2013/109756 A2 | 7/2013 |
| WO | 2013187927 A1 | 12/2013 |
| WO | 2014047650 A1 | 3/2014 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015/103547 A1 | 7/2015 |
| WO | 2015/134625 A1 | 9/2015 |
| WO | 2015/179324 A2 | 11/2015 |
| WO | 2015/189354 | 12/2015 |
| WO | 2016/010995 A1 | 1/2016 |
| WO | 2016089451 A1 | 6/2016 |
| WO | 2017089424 A1 | 6/2017 |
| WO | WO 2017/090472 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

OTHER PUBLICATIONS

Search Report issued in corresponding Chinese Patent Application No. 201680080064.4 dated Jun. 9, 2020 (English translation only).
US6,348,062, 07/2003, Hopkins et al. (withdrawn)

* cited by examiner

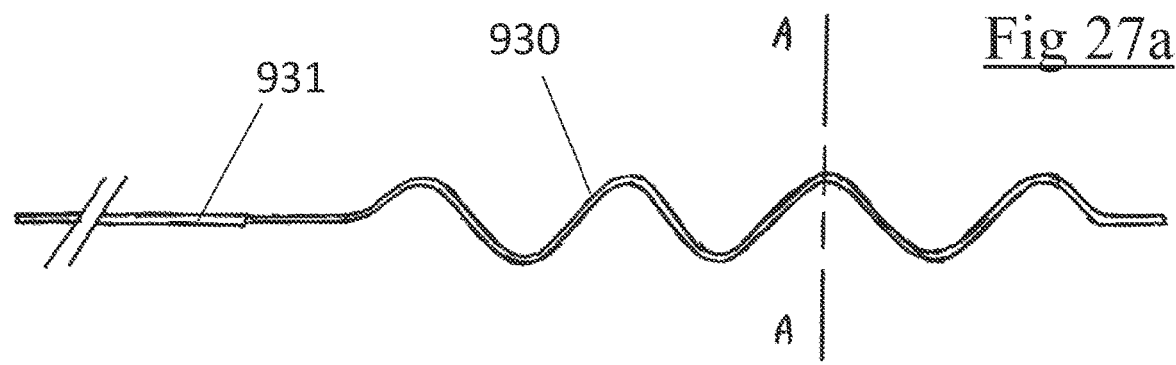
Fig 27a
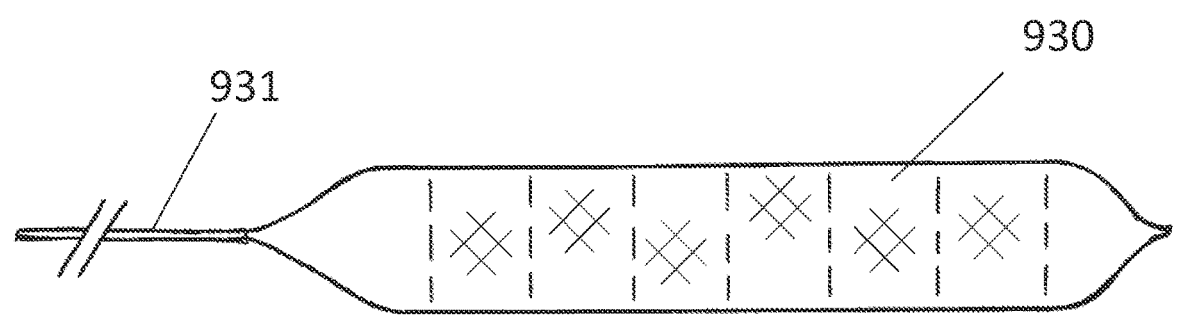
Fig 27b
Section A - A
Fig 27c
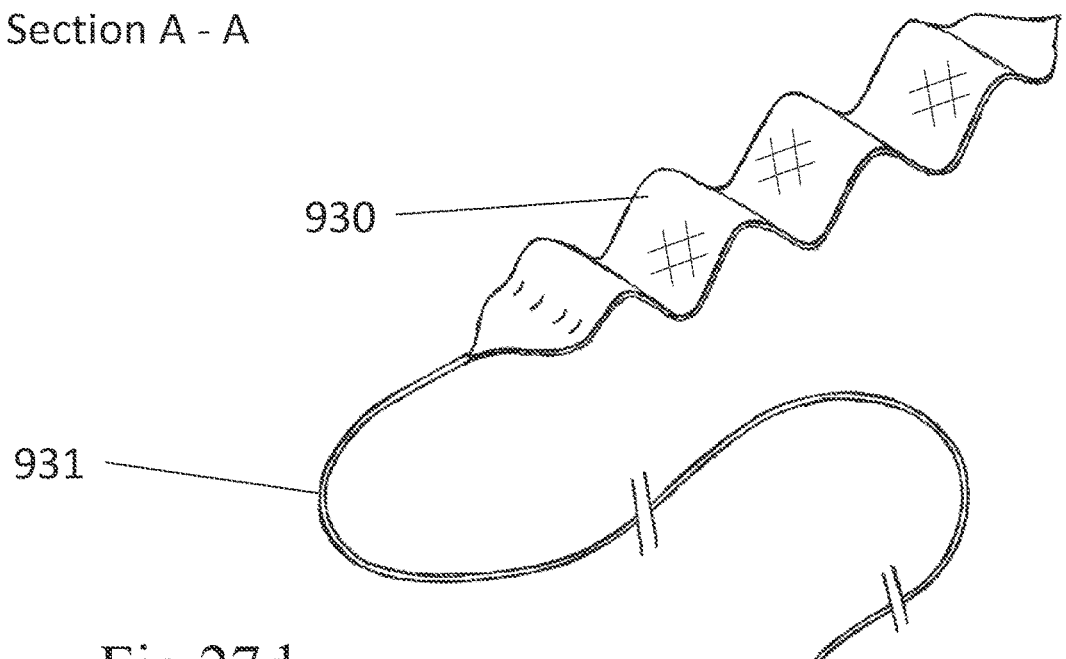
Fig 27d

Section B - B

CLOT RETRIEVAL DEVICE FOR REMOVING OCCLUSIVE CLOT FROM A BLOOD VESSEL

CROSS REFERENCE TO RELATED APPLICATIONS

This application is a continuation application of U.S. application Ser. No. 14/952,202, filed Nov. 25, 2015, and claims the benefit of U.S. Provisional Application No. 62/084,960, filed Nov. 26, 2014, each of which are incorporated herein by reference in their entirety.

FIELD OF THE INVENTION

This invention relates to devices intended for removing acute blockages from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

STATEMENTS OF THE INVENTION

According to the invention there is provided a clot retrieval device for removing occlusive clot from a blood vessel comprising a clot engaging element having a constrained delivery configuration and an expanded deployed configuration, wherein at least a portion of the device has a longitudinally extending undulating edge.

In one case the clot engaging element has a first peripheral portion, a second peripheral portion and a clot engaging section extending between the first and second peripheral portions wherein, in the expanded configuration, the peripheral portions are laterally spaced-apart and the clot engaging section extends between the peripheral portions.

In one embodiment the undulating edge has a wave-like form. The undulating edge may have a sinusoidal wave form.

In one case the device has at least two wave patterns. The wave patterns may be superimposed on one another. In one case a first pattern has a wavelength and an amplitude and the second pattern has a wavelength and an amplitude which are larger than those of the first pattern.

In one embodiment the clot retrieval device comprises an activator for modifying the wave shape. The activator may comprise at least one push wire and/or at least one pull wire.

In one case the clot engagement element comprises one or more clot gripping features.

In one embodiment, in the constrained configuration, the clot engaging section is substantially flat.

In the expanded configuration the clot engaging section may be curvilinear.

In the expanded configuration the clot engaging section may be substantially flat.

In one embodiment in the constrained and expanded configurations the clot engaging section is substantially curvilinear.

In one case in the expanded configuration, the clot engaging section is of helical or spiral form.

In the expanded configuration, the clot engaging section may be of generally s-shape.

In one embodiment the clot engaging element has two surfaces which face in generally opposite directions and one or both surfaces is engagable with clot in the expanded deployed configuration.

In one embodiment the device comprises a portion defining a flow channel for flow of blood when the device is in the expanded deployed configuration.

In one case the device comprises a proximal section, a distal section and a clot engaging section between the proximal section and the distal section wherein the proximal section is slidably movable relative to the clot engaging section. The proximal section may comprise a slidable element such as a collar and proximal struts extending from the collar and the clot engaging section comprises a proximal shaft and the collar is slidably movable relative to the proximal shaft. At least some of the struts of the proximal section may extend in a distal direction for at least partial capture of clot between the clot engaging section and the proximal struts on proximal movement of the collar relative to the proximal shaft.

In one embodiment the wave pattern has an amplitude of from 2.0 mm to 6.0 mm. The wave pattern may have a pitch of from 3.0 mm to 8.0 mm.

In one embodiment the clot engaging section comprises a plurality of cells defined by struts and crowns and at least some of the struts and/or crowns are aligned with the wave-like form to enhance embedding of clot.

In one case the clot engaging section of the device has a transverse cross section having both flat and curved sections.

In one embodiment, in the expanded configuration, at least a portion of the clot engaging section of the device is a generally spiral or helical configuration relative to a longitudinal axis. The clot engaging section may further comprise a distal tubular section. A clot fragment portion may be provided at the distal end of the tubular section.

In one embodiment the clot engaging section comprises a pair of side rails formed from cell elements to which a plurality of clot engaging strut elements are connected, the cell elements protruding from opposite sides of a plane defined by the side rails.

In another embodiment the clot engaging section comprises a plurality of segments, adjacent segments being aligned at approximately 90° to each other. At least some of the segments may be of flat shape in transverse cross section.

In all embodiments the clot retrieval device may comprise a distal clot fragment protection section.

The invention also provides a method from removing occlusive clot from a blood vessel comprising the steps of:

providing a clot retrieval device having a clot engaging section with a longitudinally extending undulating form, the device having a constrained delivery configuration and an expanded deployed configuration;

advancing a microcatheter towards and across an occlusive clot;

loading the device into the microcatheter and advancing it to a distal portion of the microcatheter;

deploying the device to embed the clot; and retrieving at least a portion of the device and the captured clot into a retrieval catheter.

In one embodiment the method comprises deploying the device within the clot.

In some cases the method comprises deploying a portion of the device between the clot and a portion of the vessel wall surrounding the clot.

In one embodiment the method comprises pulling the device proximally after deployment of the device within the clot.

The method may comprise delaying pulling of the device proximally after deployment to further embed in the clot prior to pulling of the device and the clot proximally.

In one embodiment the method comprises pulling the device proximally into a larger vessel before retrieval into a retrieval catheter.

In some cases the method comprises twisting the device to embed the device into the clot.

According to the invention there is provided a clot retrieval device for removing occlusive clot from a blood vessel comprising a clot engaging element having a constrained delivery configuration and an expanded deployed configuration, the clot engaging element having a first peripheral portion, a second peripheral portion and a clot engaging section extending between the first and second peripheral portions wherein, in the expanded configuration, the peripheral portions are laterally spaced-apart and the clot engaging section extends between the peripheral portions.

In one embodiment in the constrained configuration, the clot engaging section is substantially flat.

In one case in the expanded configuration the clot engaging section is curvilinear.

In another case in the expanded configuration the clot engaging section is substantially flat.

In one embodiment in the constrained and expanded configurations the clot engaging section is substantially curvilinear.

In one case in the expanded configuration, the clot engaging section is of helical or spiral form.

In another case in the expanded configuration, the clot engaging section is of generally s-shape.

In one embodiment the clot engaging element has two surfaces which face in generally opposite directions and either face is engageable with clot in the expanded deployed configuration.

In one case the device comprises a portion defining a flow channel for flow of blood when the device is in the expanded deployed configuration.

In one embodiment at least a portion of the device comprises an undulating edge. The undulating edge may have a sinusoidal or other wave-like form.

In one case the device has at least two wave patterns which may be superimposed. A first pattern may have a wavelength and an amplitude and the second pattern has a wavelength and an amplitude which are larger than those of the first pattern.

In one embodiment the device comprises an activator for modifying the wave shape. The activator comprises at least one push/pull wire.

In one case the clot engagement element comprises one or more clot gripping features.

The device may comprise a distal capture portion.

In one case the device is formed from a flat sheet of a shape memory material such as Nitinol.

The invention also provides a method for removing occlusive clot from a blood vessel comprising:

providing a clot retrieval device of the invention; loading the device into a microcatheter in which the device is in a constrained delivery configuration; advancing the microcatheter to an occlusive clot; deploying the device to capture the clot; and retrieving the device together with the captured clot into a retrieval catheter.

The device may be deployed within the clot to pin the clot between the device and the vessel wall. Alternatively the device is deployed between the clot and a portion of the vessel wall surrounding the clot.

BRIEF DESCRIPTION OF THE DRAWINGS

The invention will be more clearly understood from the following description of some embodiments thereof, given by way of example only, with reference to the accompanying drawings, in which:

FIG. 17b is a cross sectional view of portion of the device of FIG. 17a;

FIG. 21d shows a fragment protection region of the device of FIG. 21a;

FIG. 21e shows a portion of the mid-section of the device of FIG. 21a;

FIGS. 27a-27d are a series of views of a schematic wave shaped device;

DETAILED DESCRIPTION

Figure 1A:
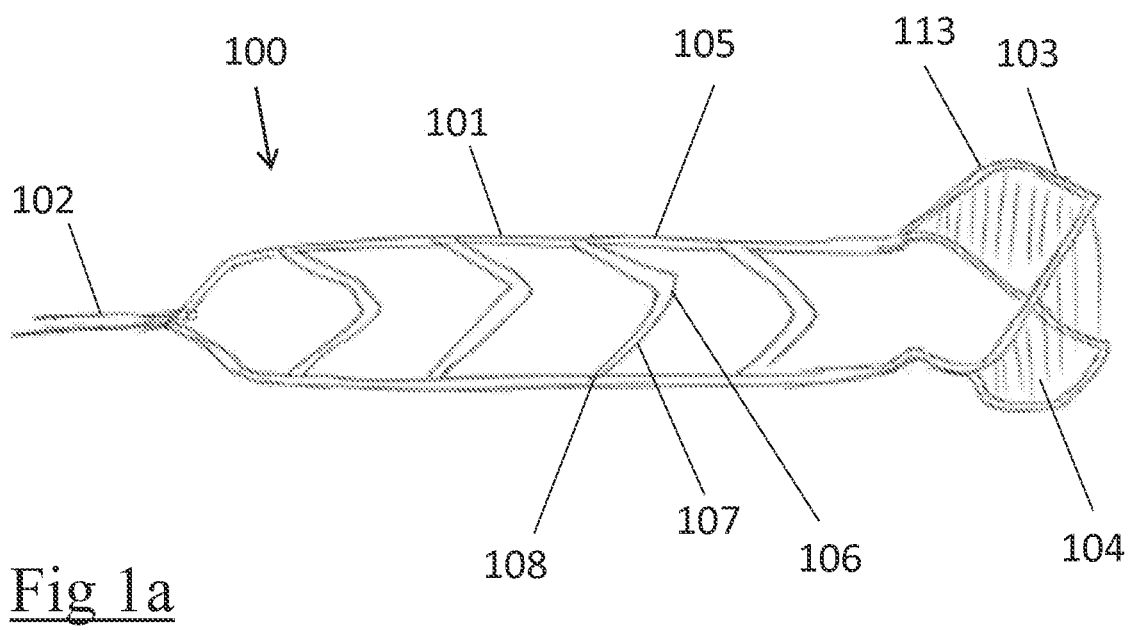
FIG. 1a is a view of a clot retrieval device of the invention.

Specific embodiments of the present invention are now described in detail with reference to the Figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are well known and are regularly used in catheter laboratory procedures. In the descriptions below that these products and methods are employed in conjunction with the device and methods of this invention and are not described in detail.

The following detailed description is merely exemplary in nature and is not intended to limit the invention or the application and uses of the invention. Although the description of the invention is in many cases in the context of treatment of intracranial arteries, the invention may also be used in other body passageways.

The expandable members of the devices disclosed are desirably made from a material capable of recovering its shape automatically once released from a highly strained delivery configuration. A superelastic material such as Nitinol or an alloy with similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a wide range of shapes as disclosed herein and may be rendered visible under fluoroscopy through the addition of alloying elements (such as Platinum for example) or through a variety of other coatings or marker bands.

Compression of the clot can alter the clot properties and make the clot less amenable to retrieval by making it firmer and "stickier" as described in our WO2012/120490A, the entire contents of which are herein incorporated by reference. The device of this invention is intended to facilitate clot retrieval by expanding between the clot and the vessel wall in such a way as to delaminate some or all of the clot from the vessel, engage with the clot over a significant surface area, and do so with minimal compression of the clot. The clot compression is minimal because the device does not need to significantly displace the clot in order to expand and engage with it. Rather the device uses the constraints of the clot itself and the vessel wall to guide its expansion, and expands within this interface region.

In its simplest form the unconstrained clot engaging portion of the device has two surfaces which face in generally opposite directions. When it is deployed within an occlusion it is constrained by the clot and vessel wall and thus must adopt a curved shape in order to expand. This curved shape can be considered to have an inside face (against the clot) and an outside face (against the vessel wall). When delivered through a microcatheter to a target site the device orientation may not be known to the user, and may not be within their power to control. An advantage of this design is that either surface of the device may become the inside or outside surface, so that the device is effectively reversible.

Figure 7:
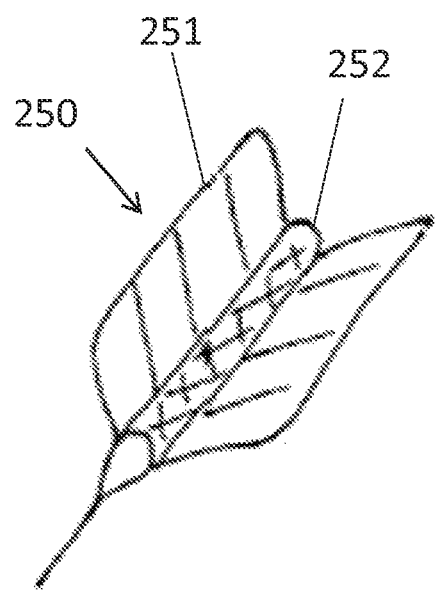
FIG. 7 is an isometric view of a clot retrieval device with a flow lumen through the device.
Figure 9:
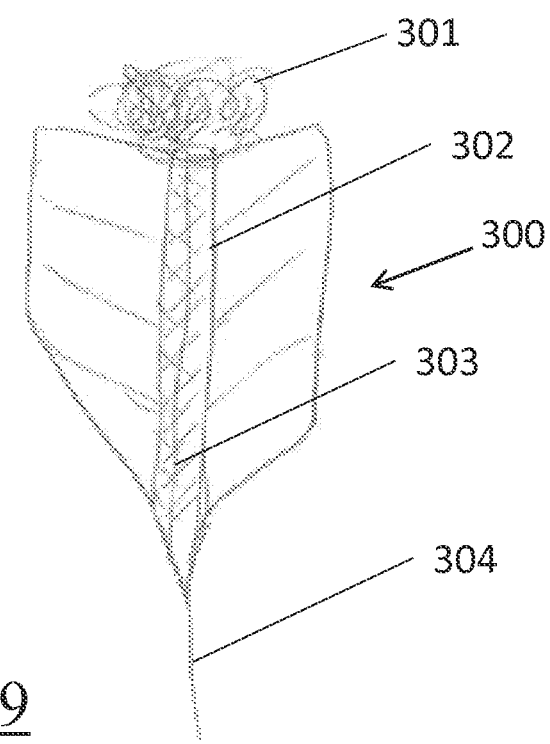
FIGS. 9 and 10 are views of further clot retrieval devices with flow channels.
Figure 10:
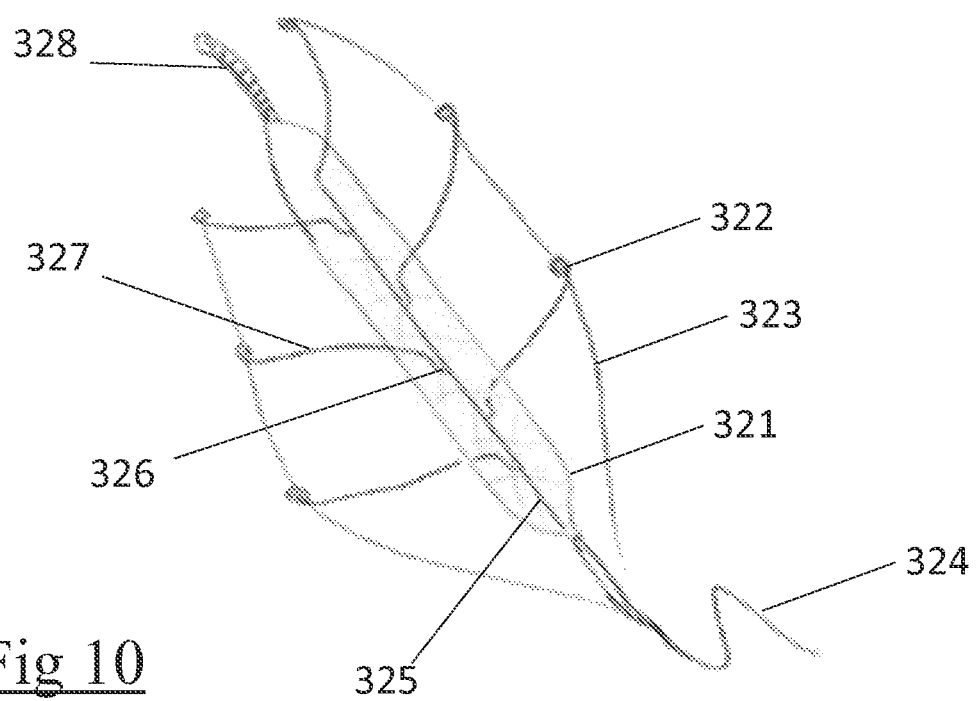

The flat device may comprise a portion that compresses an area of the clot in order to form a blood communication channel across the clot. Such a channel serves two key purposes: 1) it reduces the pressure gradient across the clot, thus reducing one of the forces that must be overcome in order to retract the clot and 2) it provides a flow path for oxygenated, nutrient carrying blood to reach the ischaemic area distal of the clot. This portion may comprise a tubular or cylindrical shape such as shown in FIGS. 7, 9, 10, or a partially cylindrical or "U" shape as shown in FIG. 19, or other shape such that a discrete portion of clot is displaced in order to create a channel free of clot from the proximal to the distal end of the clot.

All of the devices described herein may also comprise a distal fragment capture portion, such as illustrated in FIGS. 1, 9, 12 and 14. This portion is ideally deployed distal of the clot to prevent the distal migration of any clot fragments that might be liberated during retrieval.

FIG. 1a shows a clot retrieval system 100 of this invention comprising a clot engagement body 101 connected to a shaft 102 at its proximal end and to a fragment protection portion 113 at its distal end. The clot engagement body comprises a framework of axial struts 105 and cross struts 107, with the cross struts comprising proximal connection points 108 and distal crowns 106. In other embodiments alternative designs of the clot engagement body may be employed such as shown in FIGS. 3 to 10. The fragment protection portion 113 in this case comprises a strut framework 103 and a fibre matrix 104. The shape of the clot engagement body 101 in the freely expanded configuration is predominantly flat. The device has an inner and an outer side when deployed in the vessel, with the inner side 112 in contact with the clot and the outer side 111 facing away from the clot. The deployment orientation of the device defines which side is in contact with the clot and which side is facing away. The sides of the device are similar so that either side can be deployed in contact with the clot without affecting the device performance. The clot engagement body material may be Nitinol or a similar super elastic or pseudoelastic alloy, or may be stainless steel or other material with sufficient elastic strain to allow recovery upon deployment from a microcatheter. The material may be laser cut from a flat sheet of material or from a tube and then further processed to be flat.

Figure 2A:
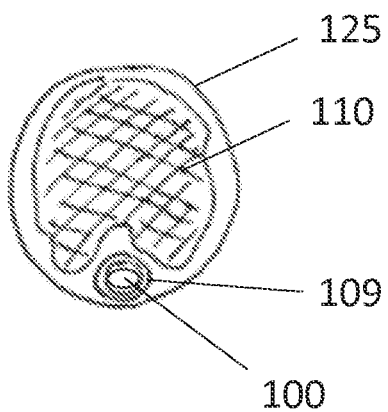
FIG. 2a is a cross sectional view of the device of FIG. 1a within a microcatheter in the region of a clot in a vessel.
Figure 2B:
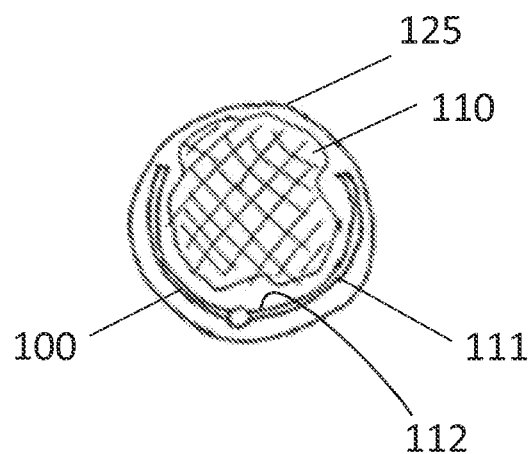
FIG. 2b is a view of the device of FIG. 2a in an expanded deployed configuration.

FIG. 2a shows a section view through an occlusive clot 110 in a vessel 125 through which a microcatheter 109 has been passed. A thrombectomy device 100 is shown within the microcatheter 109 in its collapsed delivery configuration. To introduce this device the thrombus or blood clot 110 is first crossed with a guidewire and microcatheter 109 as per standard interventional procedures. The guidewire is then removed and the device introduced as per standard procedure. The flat shape of this device allows it to expand between the clot and the vessel wall following the circumference of the vessel as shown in FIG. 2b, resulting in the device forming a 'U' shape after deployment, with the inner side of the clot engagement body 112 facing and engaging with the clot, and the outer side of the clot engagement body 111 facing the vessel wall. Positioning the device between the clot and the vessel wall reduces the contact area between the clot and the vessel wall reducing the engagement between the clot and vessel wall and subsequently the force required to dislodge the clot from the vessel. Hence by retracting the device, the clot can be dislodged and retrieved to a proximally positioned catheter or sheath, aided by aspiration if required. Alternatively the microcatheter or intermediate catheter can be forwarded to partially resheath the device causing the cell pattern of the device 100 to close, pinching the clot between the struts improving the grip between the device and the clot. The arms of the 'U' shape may also bend in towards the clot during resheathing improving the grip of the device on the clot and facilitating removal. The device and clot may be resheathed and fully removed through the intermediate catheter or the partially resheathed device and clot may be retracted with the intermediate catheter to a proximally positioned guide catheter or sheath. This may be done with or without the aid of aspiration.

Figure 1B:
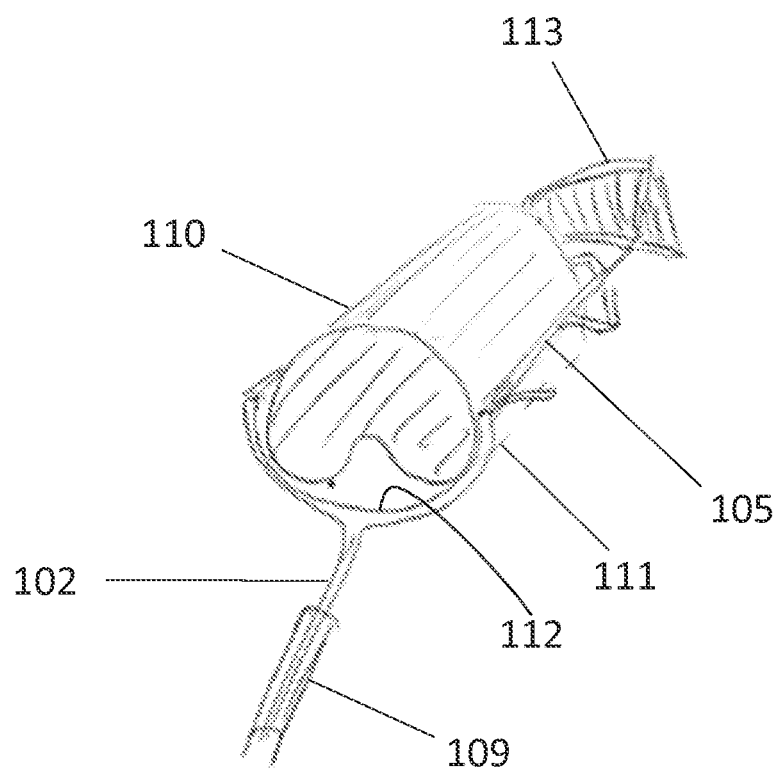
FIG. 1b is a view of another clot retrieval device including a distal fragment protection portion.

The distal end of the clot engagement body may be connected to or be integral to a fragment protection portion 113 as shown in FIG. 1b. The fragment protection portion may be flat, tubular, cone shaped or irregularly shaped in the freely expanded configuration, and may be substantially planar or occupy a volume to form a "3D" filtering body such as the mesh structure shown in FIG. 21d. In the deployed configuration in the vessel this portion provides a way of capturing embolic fragments preventing their release in the bloodstream. The fragment protection portion may be constructed from the struts of the device, threaded, knitted or braided fibres, polymer films or other material that traps embolic debris while only partially restricting blood flow.

In the embodiment shown in FIG. 1a, the clot engagement body 101 is formed of a repeating cell pattern 107 along the length of the device and is flat in the freely expanded configuration. The cut pattern may include various cell shapes and unconnected crowns.

Figure 2C:
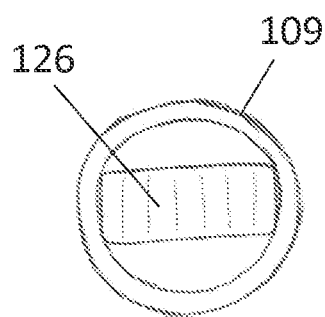
FIGS. 2c and 2d are sectional views of a microcatheter with the device of FIG. 2a in a wrapped configuration in a linear orientation and a circular orientation respectively.
Figure 2D:
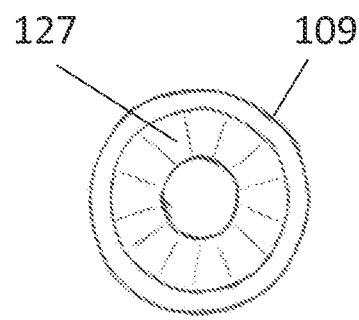

FIGS. 2c and 2d show a detailed sectional view of the microcatheter and wrapped device of FIG. 2a. When the device is in this collapsed configuration the clot engagement body may be wrapped in a circular orientation 127 as shown in FIG. 2d or the device may wrap down so that the struts align in a linear orientation 126 as shown in FIG. 2c. This collapsed linear orientation may promote the device to expand in a linear manner facilitating the expansion of the device between the clot and the vessel wall.

Figure 3A:
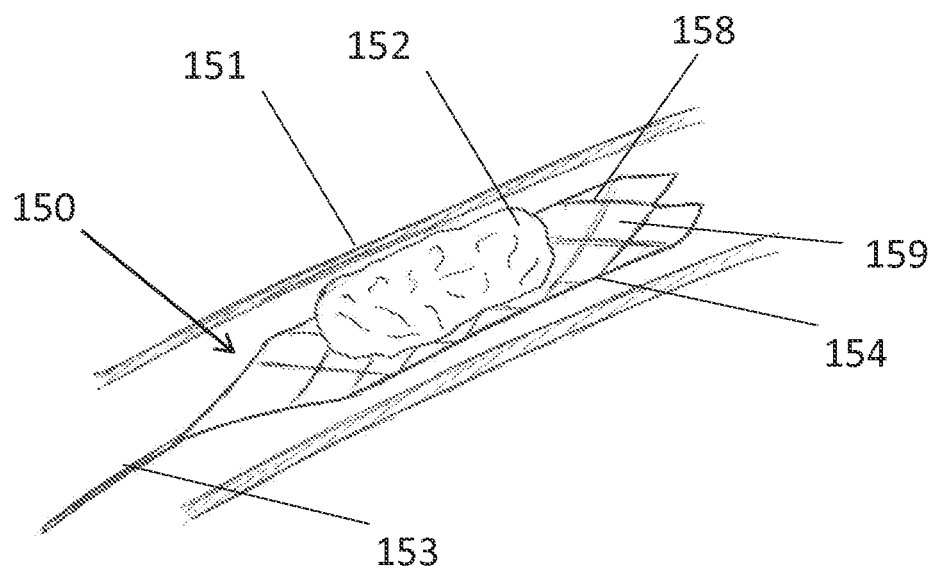
FIGS. 3a and 3b are isometric and side views of a clot retrieval device deployed in a vessel.

FIG. 3a shows an embodiment of the device (in an isometric view) which maintains a flat shape even when deployed in the vessel. This Figure shows the flat device 150 deployed in a vessel 151, and positioned under an occlusive blood clot 152. The flat section of the device 154 is connected to a proximal shaft 153 to facilitate introduction and retrieval of the device. The flat section 154 consists of a pattern of struts 158 and cells 159 which engage with and embed into the clot. The use of a flat device may improve performance in gripping and removing the clot from the vessel, as the clot is not significantly compressed by the device unlike a tubular device which exerts a radial force along the length of the clot.

Figure 3B:
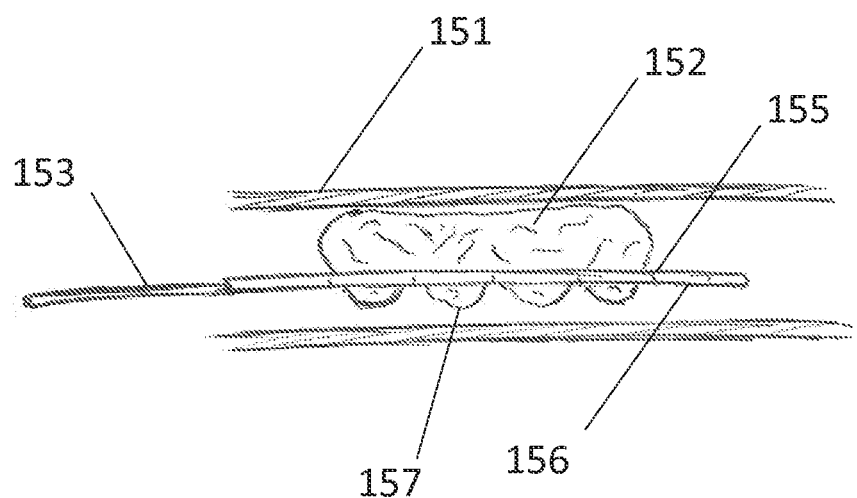

FIG. 3b shows a side view of the device and clot shown in FIG. 3a. In this view the struts 155 of the flat device 156 are shown embedded in the clot 152. This embedding causes portions of the clot 157 to protrude through the device cells improving the grip of the device on the clot. This view illustrates how significant clot compression is not required for the device to achieve good grip on the clot.

Figure 4:
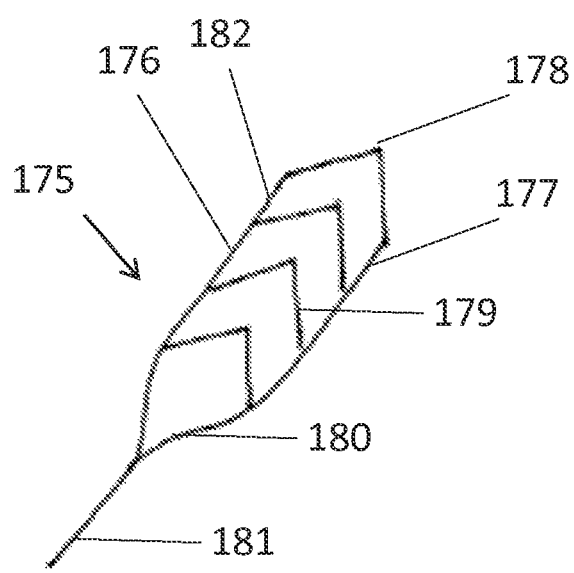
FIGS. 4, 5 and 6 are views of clot retrieval devices with various different cell shapes and cut patterns.
Figure 5:
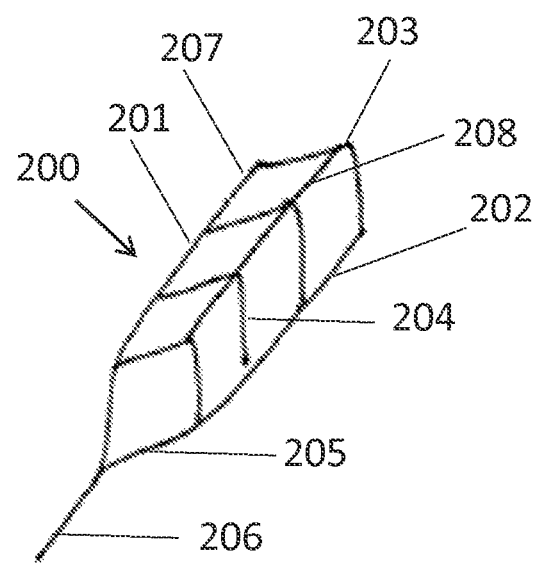
Figure 6:
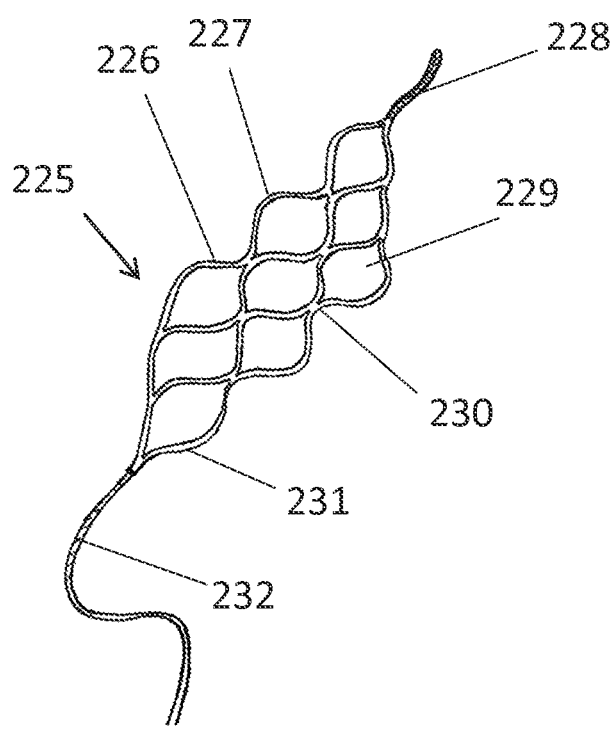

The level of strut embedding and clot protrusion into the device cells influence the level of grip the device can exert on the clot. The device cut pattern such as strut width, length, cell shape and size, crown inner diameter, floating crown design, all influence the level of strut embedding in the clot. FIGS. 4, 5, and 6 show various embodiments with different cell shapes and cut patterns. FIG. 4 shows a flat device 175 with a number of disconnected floating crowns 178. FIG. 5 shows a similar flat device 200 except the central crowns are connected together by a 'backbone' strut 208. FIG. 6 shows another iteration of the flat device with multiple cells 229 connected along the length of the flat device 225.

Figure 8A:
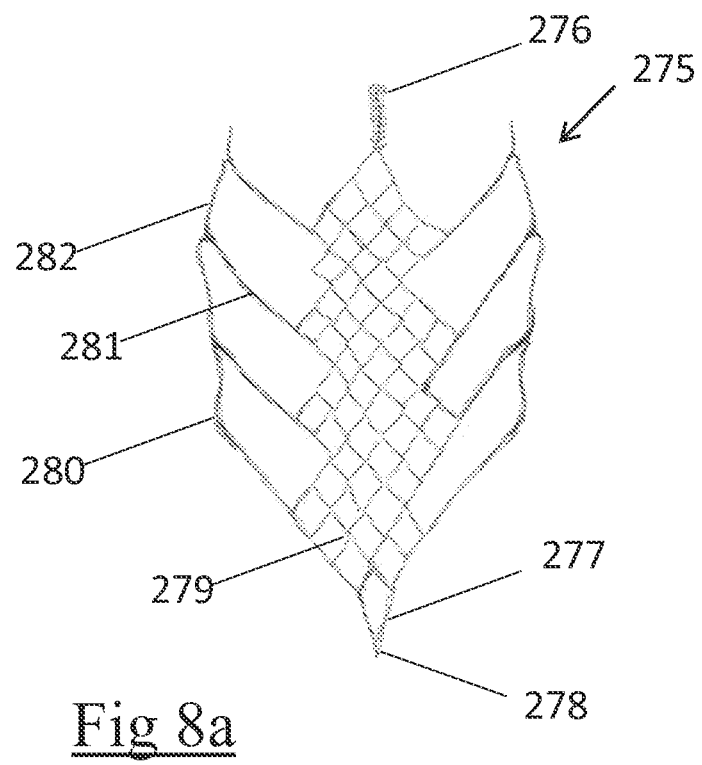
FIGS. 8a and 8b are views of a flat pattern clot retrieval device with a circular or u-shaped channel.
Figure 8B:
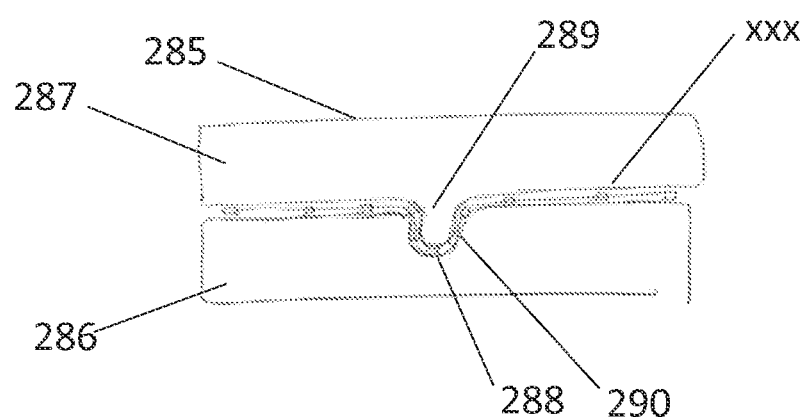

In another embodiment shown in FIG. 7 the flat pattern is combined with a tubular mid-section 252 which provides a flow lumen through the device on initial deployment in the clot. This flow lumen 252 may be formed by an integral or by a separate tubular component. On deployment the flat section of the device still expands between the clot and the vessel wall each side of the flow lumen. FIGS. 8a and 8b shows an alternative flat pattern 275 which can be heat-set to form a circular or U shape channel 288 in the device. This can be achieved by clamping the device in a fixture 285, such as that shown in FIG. 8b, prior to heat treatment. The cell pattern shown 280 has different cell sizes and shapes for the outer flat section 281 and the central U channel 279 to minimise the risk of the clot blocking the flow in the central channel on deployment, and to improve device flexibility.

FIG. 9 illustrates a device 300 which is very similar in design to device 250 of FIG. 7, but also comprises a distal mesh component 301. This distal mesh component may be attached to the distal end of the tubular mid-section 302 or to a connecting member 303 which runs through the tubular member and connects to a proximal elongate shaft 304. This distal mesh component 301 may be formed from one or more filaments or fibres, which may be monofilaments or multifilament's, and may be of a high strength polymeric material such as Ultra-High Molecular Weight Polyethylene (UHMWPE), Liquid Crystal Polymer (LCP), Polyethylene (PE), Polyethylene Terephthalate (PET), Polyamide (PA), Polyethylene Naphthalate (PEN) or an Aramid, or may be of a metal material. If of metal material the fibres or filaments are preferably formed from a shape memory or superelastic material such as Nitinol, so that they can recover form a compressed configuration within a microcatheter to form a dense mesh of a diameter approximately equal to that of the vessel in which the device is deployed so as to prevent the distal migration of clot fragments.

In the embodiment shown in FIG. 10 the device consists of a central tubular component 321 providing a flow lumen, combined with radiating arms 327 along the length of the device. These radiating arms 327 are connected to the proximal shaft 324 through connecting member 325, and are connected to a fibre or wire 323 at connection points 322 and expand between the clot and vessel wall on deployment, reducing friction between the clot and the vessel wall. During retraction the fibres provide additional engagement with the clot and help to grip and dislodge the clot from the vessel, and retrieve it to the proximal catheter or sheath. This Figure also shows the proximal shaft 324 and a distal radiopaque tip 328 on the device.

Figure 11A:
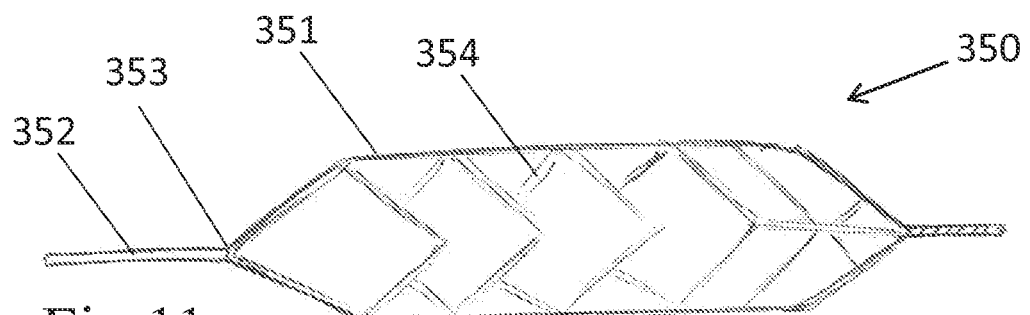
FIGS. 11a to d illustrate another clot retrieval device having a portion with a flat configuration.
Figure 11B:
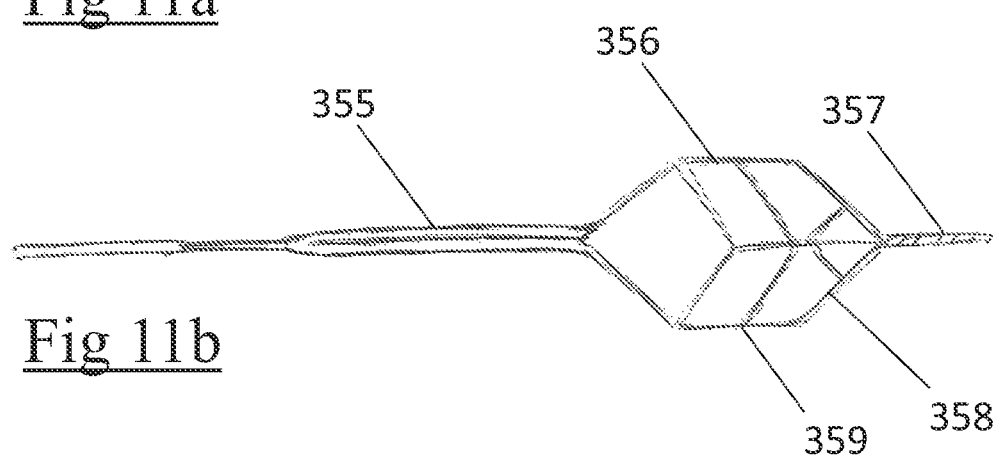
Figure 11C:
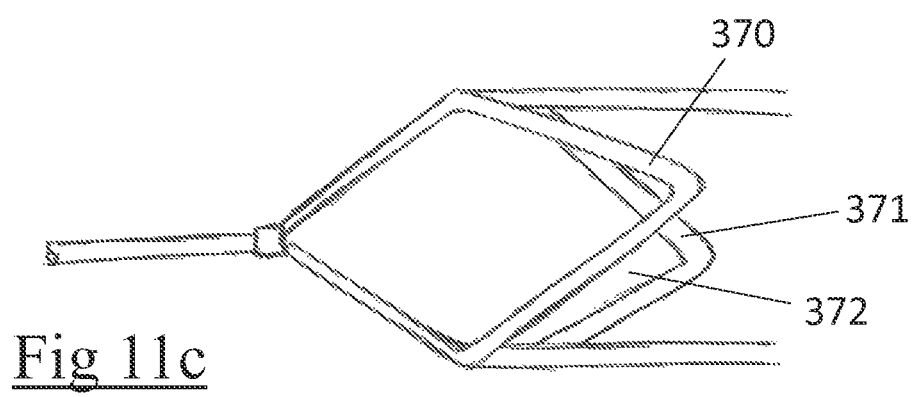
Figure 11D:
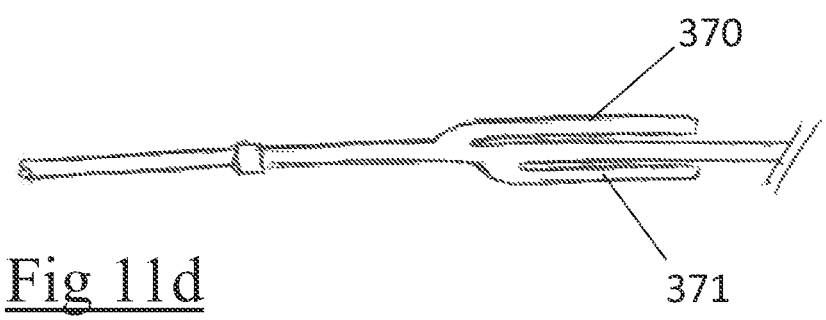

In another embodiment of the device as shown in FIGS. 11a-d, a flat section of the device 355 is formed by heat-setting a portion of a tubular device into a flat configuration, FIG. 11b. The section of the device heat-set into a flat configuration may be adjacent to a tubular section or cone section of the device or in between two tubular sections, or be the full length of the device. This forming method can result in the flat section containing 2 layers of struts and crowns 370 and 371. The cut pattern of the device 354 prior to flattening may be configured so that after reshaping to a flat configuration both layers have the same strut pattern with struts and crowns aligned on top and bottom. Alternatively the strut pattern may be designed so that the struts do not align but leave spaces for the clot to embed in between the struts 372. This allows the struts to pinch the clot, FIG. 11c, when the device is retracted or partially resheathed into an intermediate catheter, guide catheter or microcatheter. The clot pinching by the struts increases the grip of the device on the clot and improves the ability of the device to dislodge difficult clots. This construction method facilitates combining the flat section 355 with a tubular 356 and cone shaped 358 distal fragment protection section.

Figure 12:
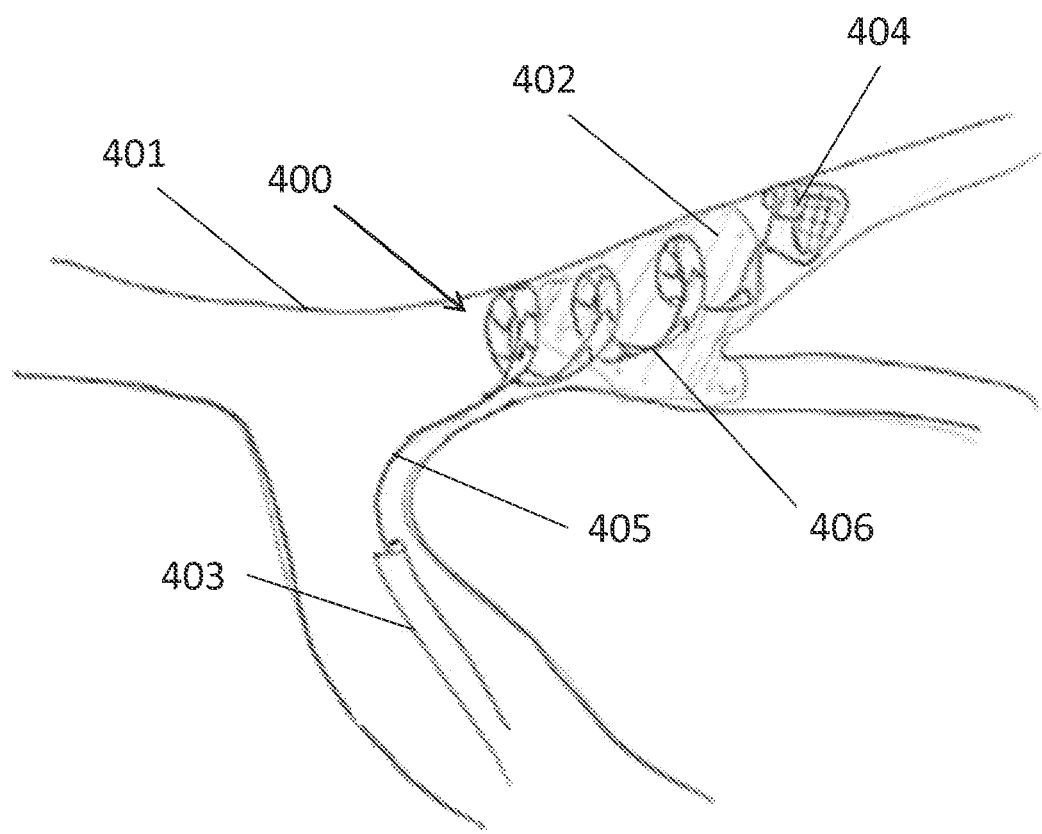
FIGS. 12 and 13 illustrate a clot retrieval device which is in a helical shape.
Figure 13:
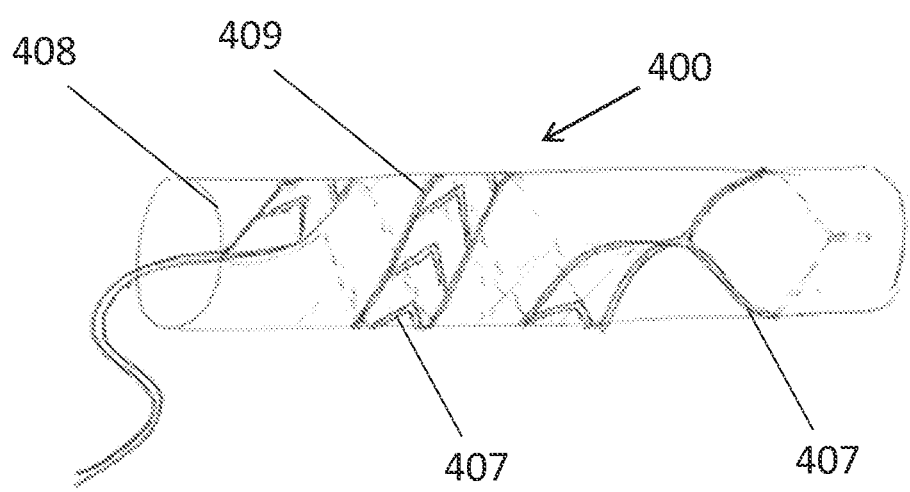

In another embodiment of the device shown in FIGS. 12 and 13, the device 400 is formed in a helical shape where the body of the device conforms within the vessel so that it is predominantly in contact with the vessel wall along the full length of the device. The centreline of the device also forms a helical path in this case. This device can be formed by laser cutting the required strut pattern 409 from a tube or by cutting a flat sheet and then wrapping the flat part around a cylinder 408 prior to heat-setting. Therefore the device has a similar shape to wrapping a wide ribbon around a cylinder.

When viewed along the vessel axis, this device does not impinge significantly into the vessel lumen. By positioning the device between the clot and the vessel wall, the area of clot in contact with the vessel wall is reduced which minimises the friction between the clot and the vessel and reduces the dislodgement force. This device also has the benefit of not compressing the clot when the clot is inside the lumen of the device which makes the clot easier to dislodge. Typical stentriever devices engage the clot so that the clot is predominantly positioned on the outer radial surface of the device with partial protrusion of the clot into the open cells of the cut pattern between the struts. The device of the invention facilitates the entire clot being positioned within the lumen of the device without the clot being compressed by the struts and crowns. During aspiration with a syringe or vacuum pump the engagement of the clot on the device with typical stentrievers can inhibit the flow of the clot into the aspiration or intermediate catheter due to the engagement between the clot and the device struts. This embodiment of the device facilitates aspiration as the clot is fully in the lumen of the device and the struts do not impede the flow path of the clot into the aspiration catheter.

Figure 14A:
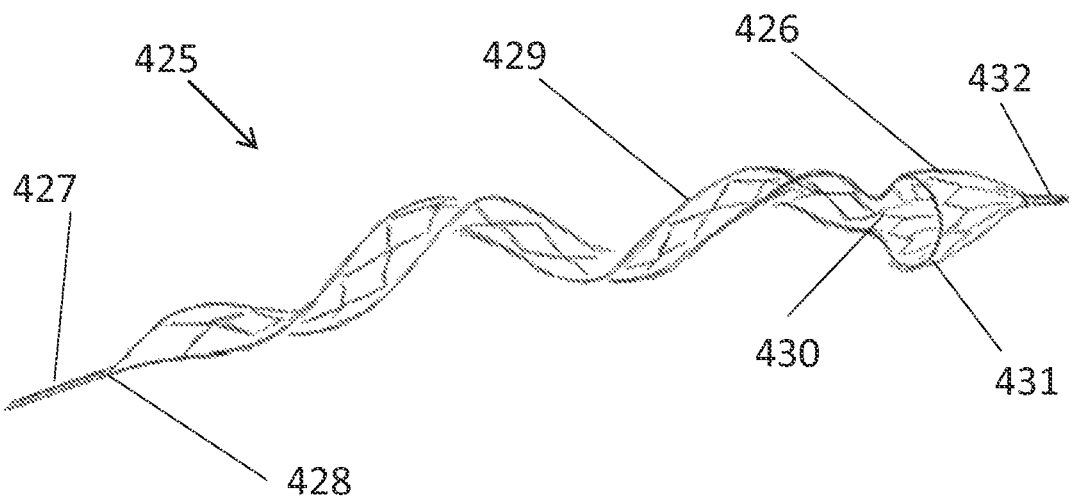
FIGS. 14a, 14b and 15 illustrate another helical device with a distal protection portion.

FIG. 14a illustrates another embodiment 425 of a helical device of this invention similar to device 400 shown in FIGS. 12 and 13. This device comprises an elongate generally planar framework 429, which may be made from wire or from interconnected strut elements. Framework 429 is configured in a spiral or helical shape and is connected at its proximal end 428 to an elongate shaft 427, and at its distal end 430 to a fragment protection section 426, which itself terminates in a distal tip 431.

Figure 14B:
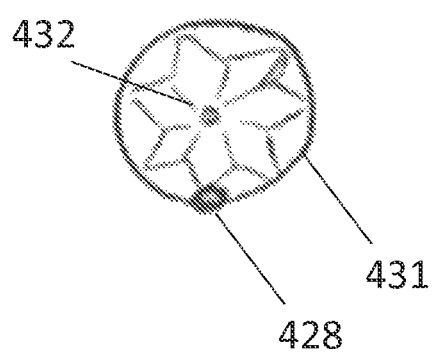

FIG. 14b shows an end view of the device of FIG. 14a, clearly illustrating the fragment protection section 426 which is intended to minimise the risk of losing embolic material during clot dislodgement and retrieval.

Figure 15:
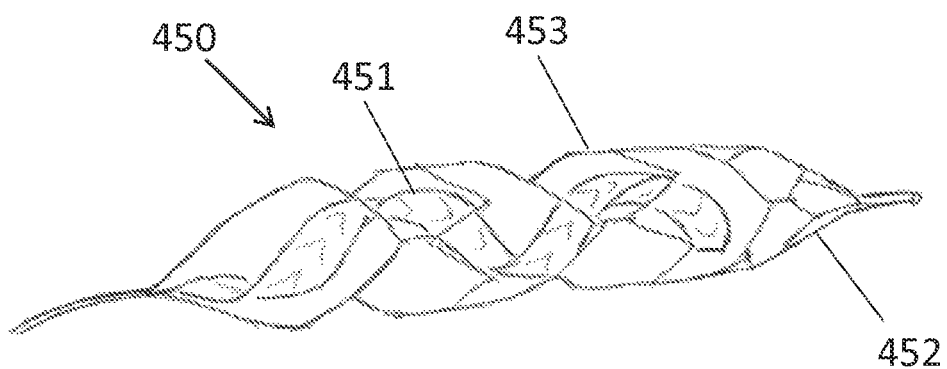

The helical shaped component can be used as an outer cage to engage and remove the clot, or as before, as shown in FIG. 15, can also be used as an inner component 451 within an outer cage 453 providing a flow channel for the restoration of flow when deployed within the clot.

Figure 16:
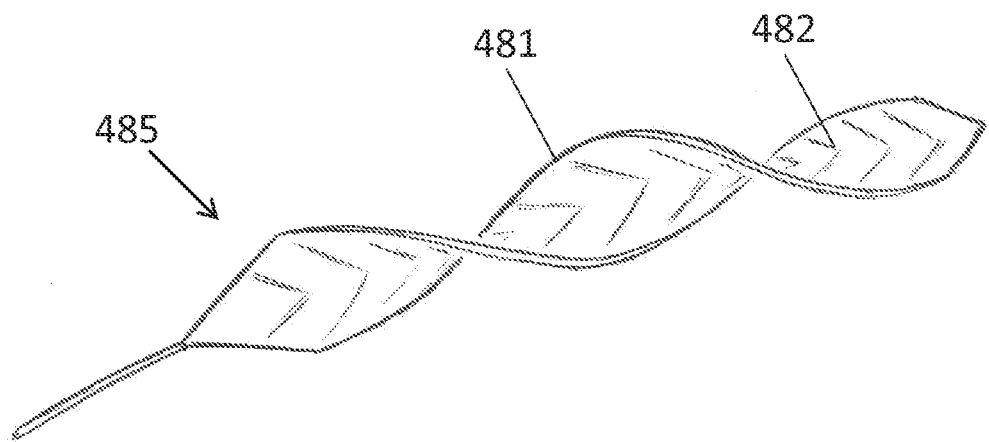
FIG. 16 illustrates another clot retrieval device which is twisted along the length of the device.

An additional embodiment shown in FIG. 16 shows a flat device 485 which has been twisted along the length of the device. The device comprises a framework of struts 482. In an unconstrained configuration, the centre-line of the device is a straight line and the sides 481 of device are twisted around this axis in a double helix shape similar to a twisted ladder or ribbon. As in all the designs described here, this component could be used to engage the clot for dislodgement and retrieval or it could be part of an assembly and act as an inner component providing a flow channel for immediate restoration of flow on deployment. When acting as a flow channel, this component is positioned inside an outer cage which predominantly engages the clot.

Figure 17A:
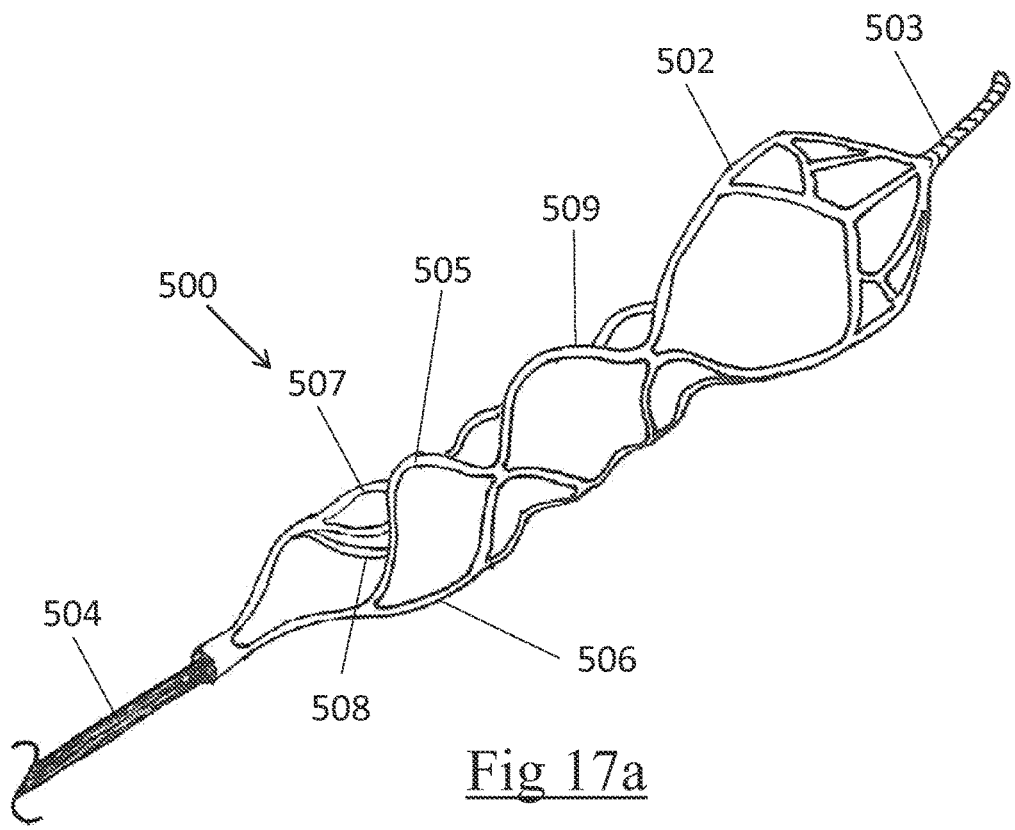
FIG. 17a is an isometric view of another clot retrieval device of the invention.
Figure 17B:
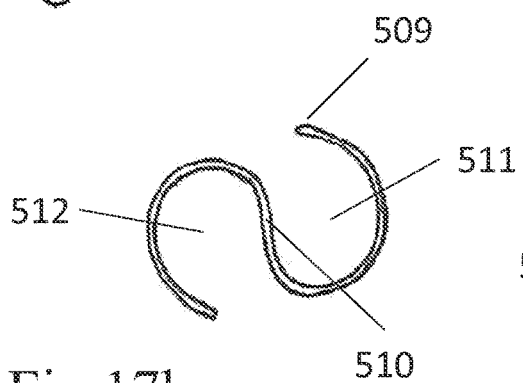
Figure 17C:
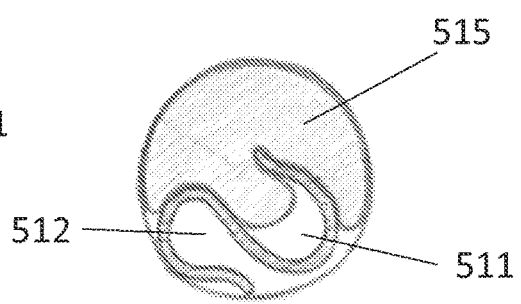
FIGS. 17c to e show the device of FIGS. 17a and b in use.
Figure 17D:
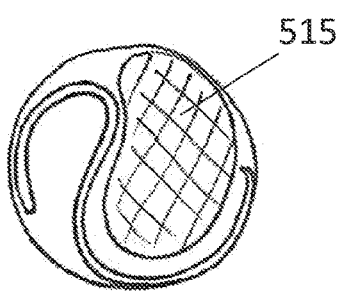
Figure 17E:
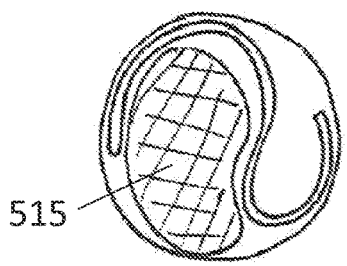

The device 500 shown in FIG. 17a-e has a body section 501 and a distal fragment protection section 502. When viewed along the vessel axis the cross section of the body section has an 'S' shape as shown in FIG. 17b-e. In the unconstrained configuration, the outer arms of the 'S' shape 509 are curved with the mid-section 510 forming a diameter. This device diameter can vary in length typically in the range of 0.5 mm up to 10 mm. The device is designed so that on deployment in the clot 515, the clot engages with the cell pattern on the outer parts of the device, and can also protrude into the opening 511 between the device arms and diameter section potentially filling one side of the 'S' shape. The other side of the 'S' shape provides a protected flow lumen 512 for restoration of blood flow on deployment of the device. Both sides of the 'S' shape are equivalent and either side can be deployed in contact with the clot, as shown in FIGS. 17d and 17e. The side of the device in contact with the clot will depend on the deployment orientation. To dislodge the clot the device is retracted back to a proximally positioned balloon occlusion guide catheter, standard guide catheter or sheath, under aspiration. Alternatively an intermediate or distal access catheter may be used to apply distal aspiration and the device can be fully or partially resheathed into the catheter. During resheathing the clot protruding into one side of the 'S' profile can be pinched and gripped by the arms of the 'S' shape improving the grip of the device on the clot. The clot pinching can also be achieved by partial resheathing of the device into the microcatheter.

The edges 505 of the arms 509 of the 'S' shape may be profiled or curved to improve clot engagement and increase clot protrusion into one side of the device.

Figure 18A:
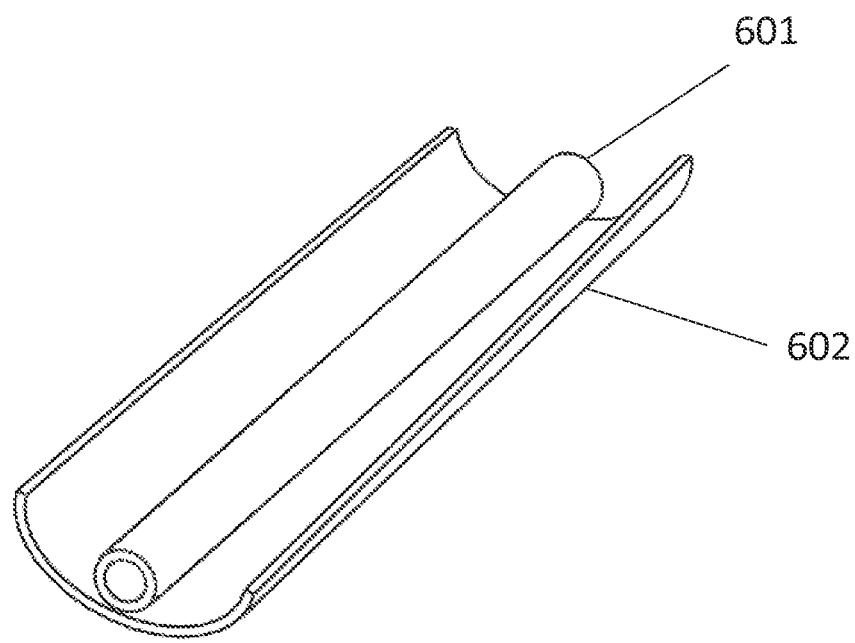
FIGS. 18a and 18b illustrate further clot retrieval devices with flow channels in which details of cell pattern(s) and strut(s) are omitted.
Figure 18B:
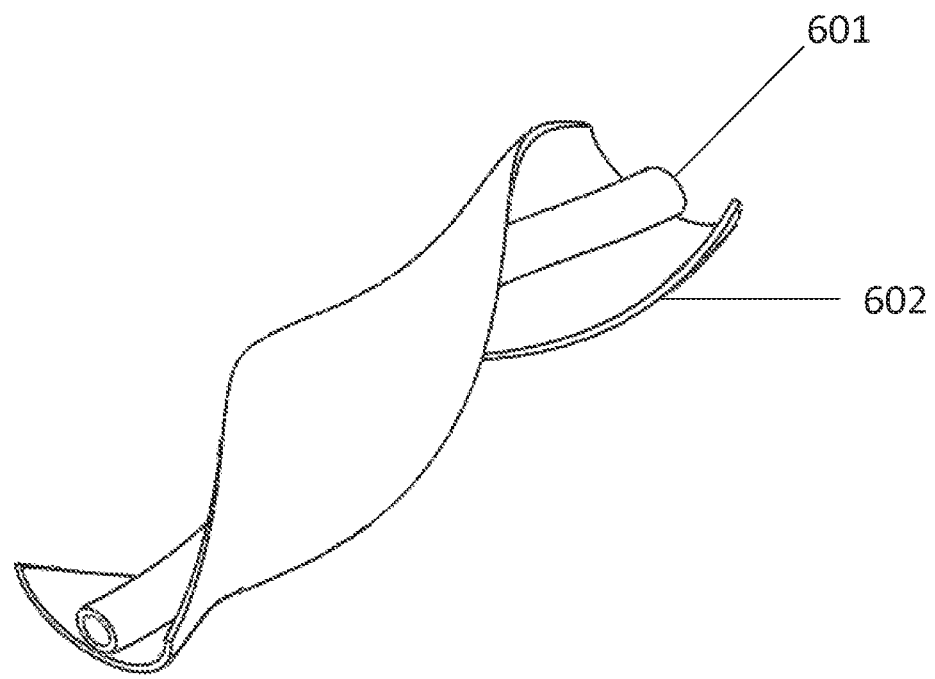

FIGS. 18a and 18b show other embodiments of the device where a flow channel 601 and 'C' shaped outer cage 602 are shown in a straight configuration (FIG. 18a) and a helical configuration (FIG. 18b). These images show only the outlines of both components and do not show the details of the cell pattern or struts which may be any of those described and/or illustrated herein.

Figure 19A:
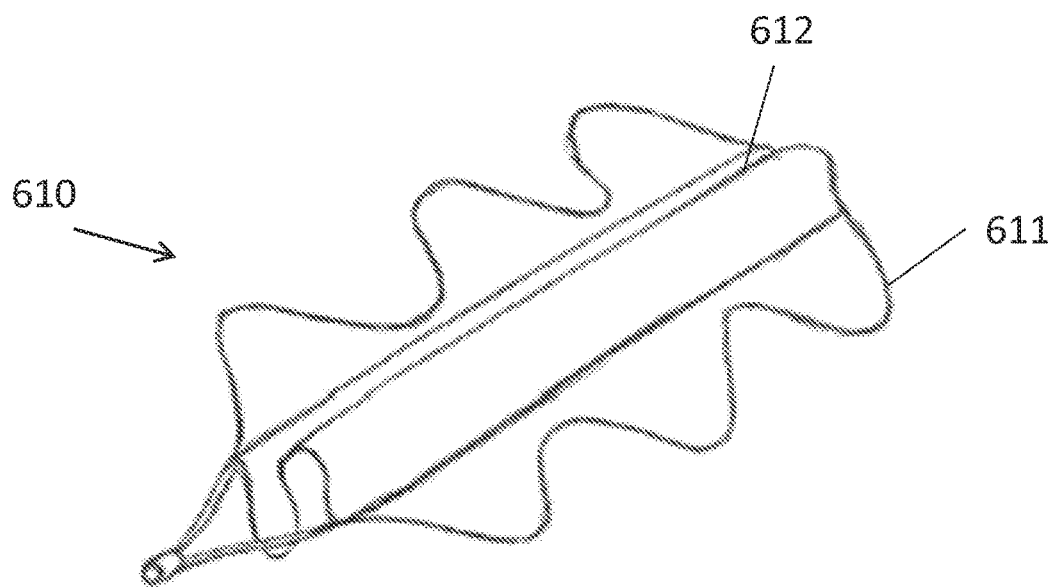
FIGS. 19a-19c illustrate a clot retrieval device with a wave-like edge combined with tubular s-shape or u-shape central sections.
Figure 19B:
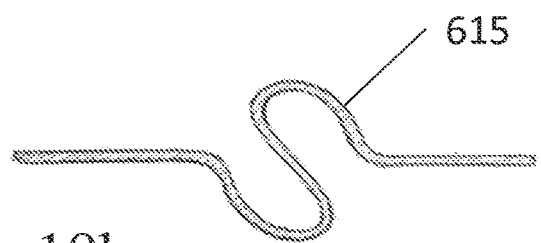
Figure 19C:
Figure 20:
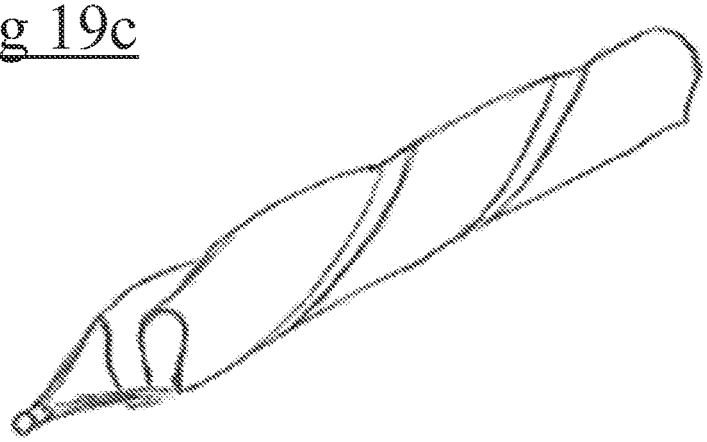
FIG. 20 shows a clot retrieval device with an s-shape cross section which spirals along the length of the device.

In an alternative embodiment of the design shown in FIG. 19a-c, the flat portion of the device 610 has a sinusoidal or wave like edge 611 combined with a tubular, 'S' shape or 'U' shape central section 612 as shown in the cross sectional views in FIGS. 19b and 19c. The wave like edge 611 to the flat portion may improve the flexibility of the device as it is deployed or retracted around tortuous bends within the vasculature. The 'S' cross sectional shape 615 has the benefit of always providing a flow lumen through the device to restore blood flow on deployment in the clot regardless of orientation. Regardless of which side of the device is deployed in contact with the clot, a protected channel exists which allows blood flow through the device. The 'S' shape increases the clot contact area between the clot and the device improving the ability of the device to engage with and dislodge the clot. The 'S' cross section shape may also spiral along the length of the device as shown in FIG. 20. The 'S' shape also provides additional clot grip during partial or full resheathing of the device by the intermediate catheter as clot within the arms of the 'S' is pinched between struts and the intermediate catheter tip.

Figure 21A:
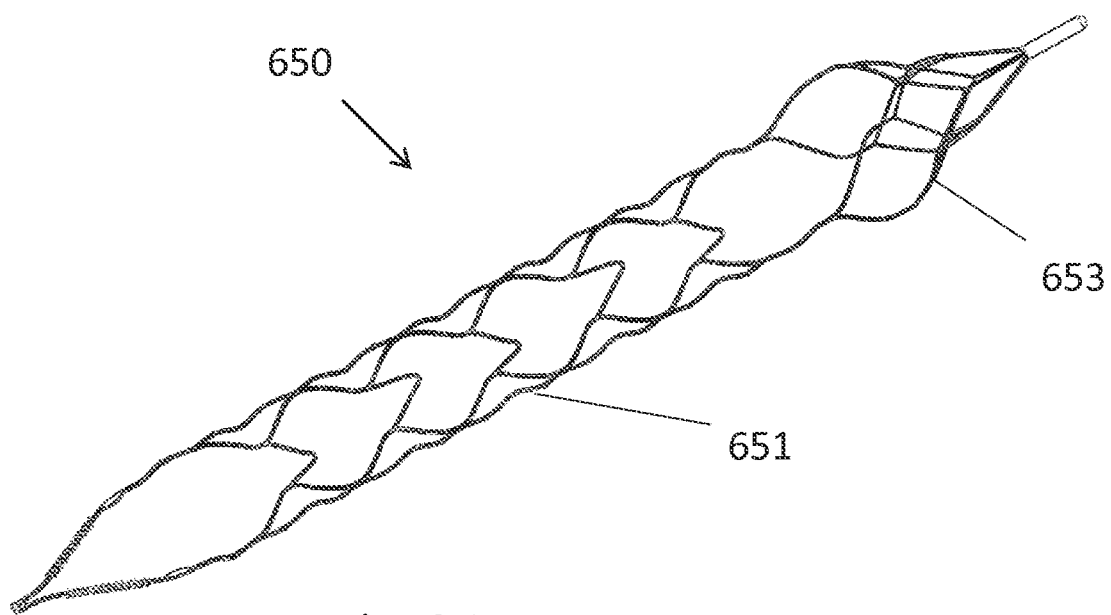
FIGS. 21a-21c are views of another clot retrieval device with a flat mid-section.
Figure 21B:
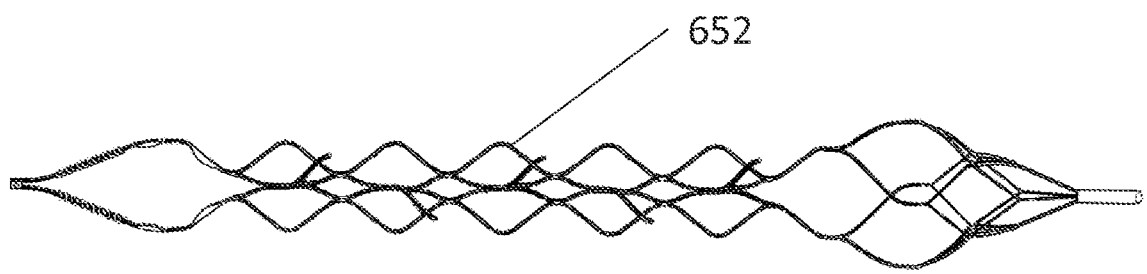
Figure 21C:
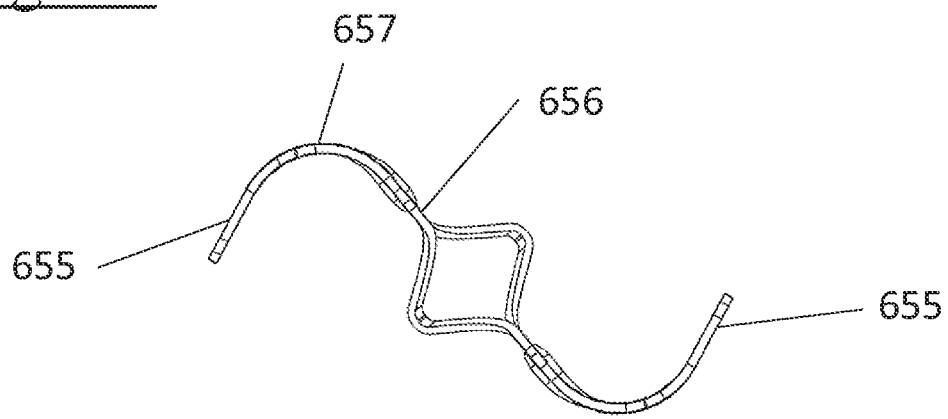

FIG. 21a-c shows another embodiment of the device 650 in which a mid-section 651 is formed so that when viewed from the side, FIG. 21b, perpendicular to the vessel axis, it has a sinusoidal or wave shape 652. The device consists of two sides as before with one side facing into or in contact with the clot and the other side generally facing away from the clot. If the device is inverted, the side previously facing into the clot would then be facing away from the clot.

Forming the device in a wave shape varies the contact pressure between the clot and the device along the length of the device, reducing the compression of the clot by the device in places. The device can also elongate when placed under tension such as during the dislodgement of a clot from the vasculature. This minimises the linear compression of the clot and may elongate the clot during dislodgement reducing the friction between the clot and the vessel wall and hence the dislodgement force required by the device to remove the clot.

In another embodiment of the device shown in FIG. 21c, the device has curved edges 655 when viewed along the axis of the vessel. This has the benefit of increasing the area of the device in contact with the vessel wall reducing the contact pressure applied to the wall by the device. When viewed along the vessel axis, the curved edges 655 can be tangential to a curve 657 which is tangential to flat section 656 or part of a continuous curve so that the cross sectional shape is that of a flattened 'S'. This cross sectional shape has the benefit of an improved wrapping profile in the collapsed configuration. It also facilitates the curved sections of the device pinching the clot during partial or full resheathing into the intermediate catheter, guide catheter, sheath or microcatheter.

Figure 21D:
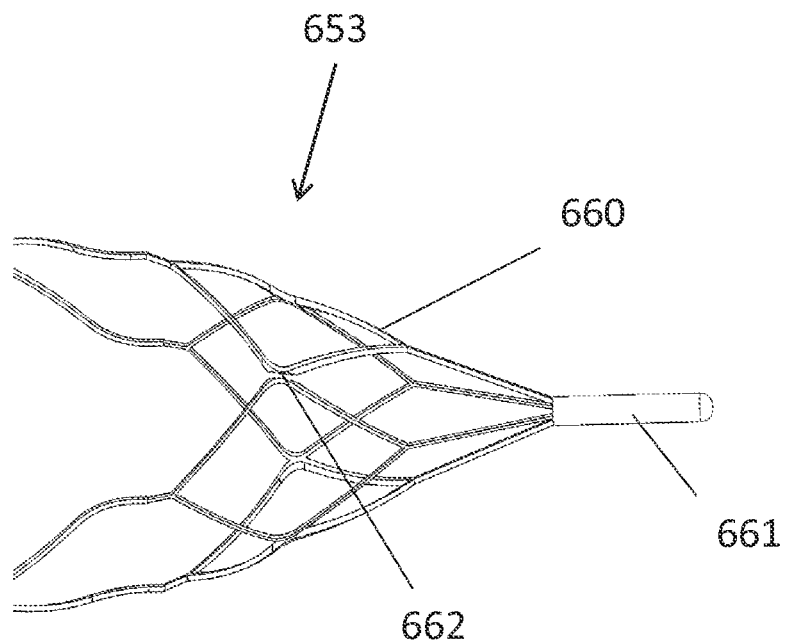

FIG. 21d shows a view of the fragment protection cone 653 which is formed of laser cut nitinol struts 660 and may also include polymer fibers to increase the density of the fragment protection mesh. This cone may be formed by laser cutting a flat sheet and then wrapping in a cone shape. The sheet material may then be joined together at the seam 662, for example by laser welding. Alternatively the seam may be left unconnected to facilitate ease of cleaning during the procedure if the device needs to be reused. A radiopaque coil 661 or tip may also be added to the cone for increased visibility under fluoroscopy.

Figure 21E:
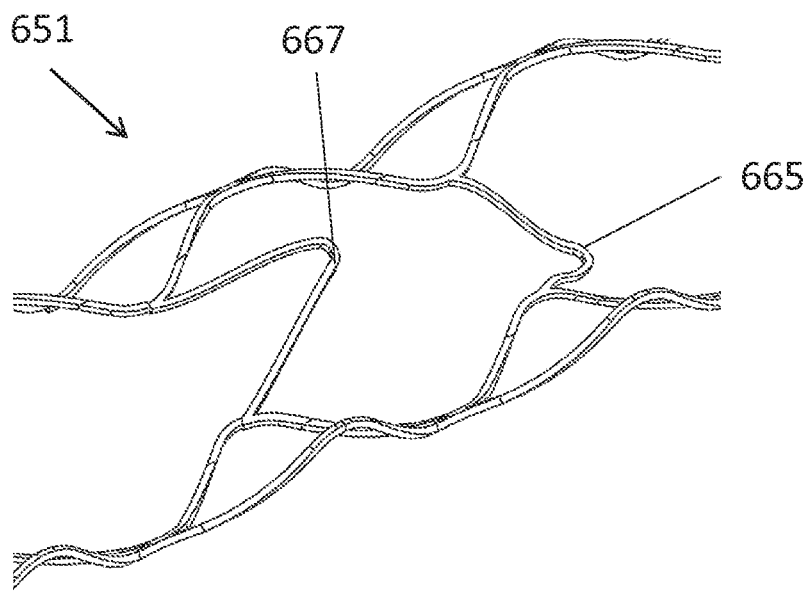

A portion of the mid-section 651 is shown in FIG. 21e. This view shows the floating or unconnected crowns 665 and 667 which are formed to be out of plane with the remainder of the mid-section. These crowns contact the clot on deployment improving the ability of the device to dislodge the clot. In addition these crowns maintain contact with the clot as the device is retracted around a bend providing a particular benefit in retrieving the clot past bends and branches.

Figure 22A:
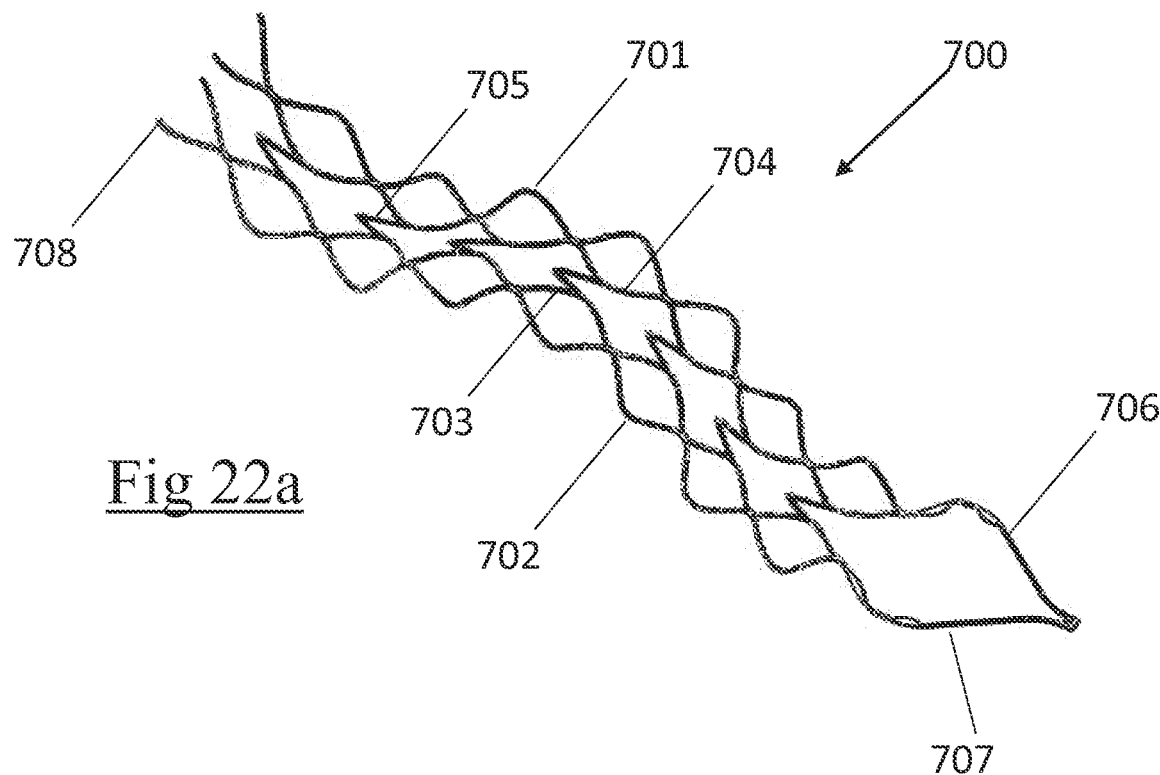
FIGS. 22a-22c are isometric, plan and side views of a clot engaging portion of another device according to the invention.
Figure 22B:
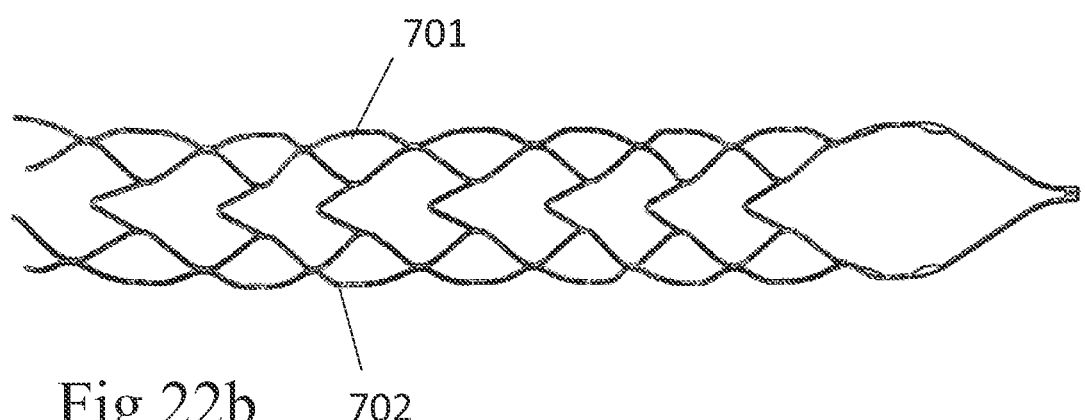
Figure 22C:
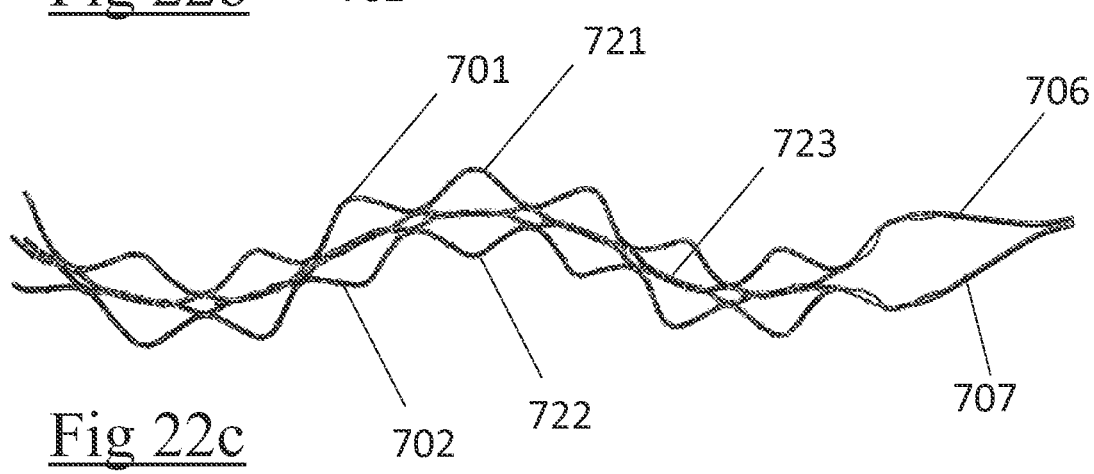

FIG. 22a-c show an isometric, plan and side view respectively of a clot engaging portion 700 of another device of this invention.

Device 700 comprises proximal struts 706 and 707, which may be connected to a proximal elongate member (not shown). These proximal struts are connected distally to a network of strut elements, comprising side rails 701 and 702, floating cells 705, and connecting arms 703.

Various devices of the invention such as the device 700 may have two superimposed wave patterns: a first pattern of a relatively short wavelength and amplitude superimposed on a second pattern of a relatively long wavelength and amplitude. The device strut elements are configured in such a way as to impart a relatively strong restorative force to the first wave pattern to restore it from its relatively straight delivery configuration within a microcatheter to an undulating or sinusoidal configuration when deployed within a clot in a blood vessel. This allows the device to engage with the clot and grip it gently but securely for initial dislodgement. In order to retrieve the clot it may be necessary to retract the device and clot proximally into larger vessel diameters before they can be safely withdrawn into a large receiving catheter. The second wave pattern assists the device in retaining control of the captured clot during this retraction. This large amplitude pattern effectively enables the device to size itself to the vessel as the vessel size increases, and thus enables the device to remain in contact with the clot in larger more proximal vessel diameters in which the clot might otherwise become dislodged from the device.

The two different wave patterns can be seen most clearly in side view in FIG. 22c, where the effective centerline of the entire clot engaging portion follow the large amplitude curve 723, and the two side rails 701 and 702 of the device follow shorter pitch sinusoidal patterns 721 and 722 respectively.

Figure 23A:
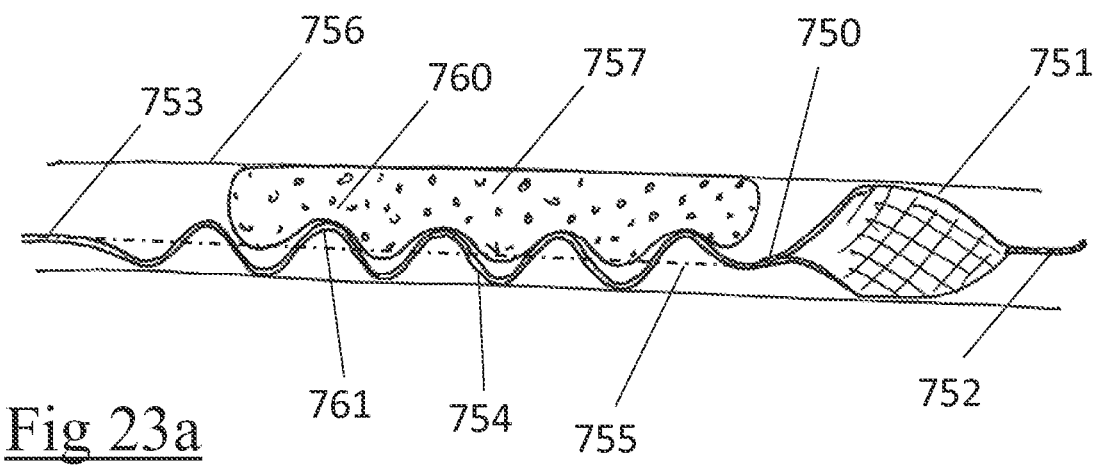
FIGS. 23a and 23b are schematic views of a clot retrieval device, in use.

FIG. 23a shows a schematic view of a device 750 engaged with a clot 757 in a vessel segment 756. Device 750 is similar to device 700 but has an additional fragment protection portion 751 with a distal tip 752 appended to its distal end. Device 750 comprises a body section 754 which may be connected at proximal end 753 to an elongate shaft (not shown). Body section 754 is configured to expand into an undulating wave somewhat sinusoidal wave pattern when deployed as shown in FIG. 23a. This wave pattern comprises peaks 761 which cause local compression of the clot in discrete regions adjacent said peaks such as region 760 shown, but causes minimal overall compression on the bulk of the clot body. Thus the overall properties of the clot are relatively unchanged by the action of the device on deployment, but discrete regions 760 are compressed and gripped by the device. This compression causes some local dehydration of the clot, increasing its coefficient of friction and thus increasing its grip and engagement with the device. But because the bulk of the clot remains uncompressed by the device the frictional engagement of the clot with the vessel is not significantly increased.

Figure 23B:
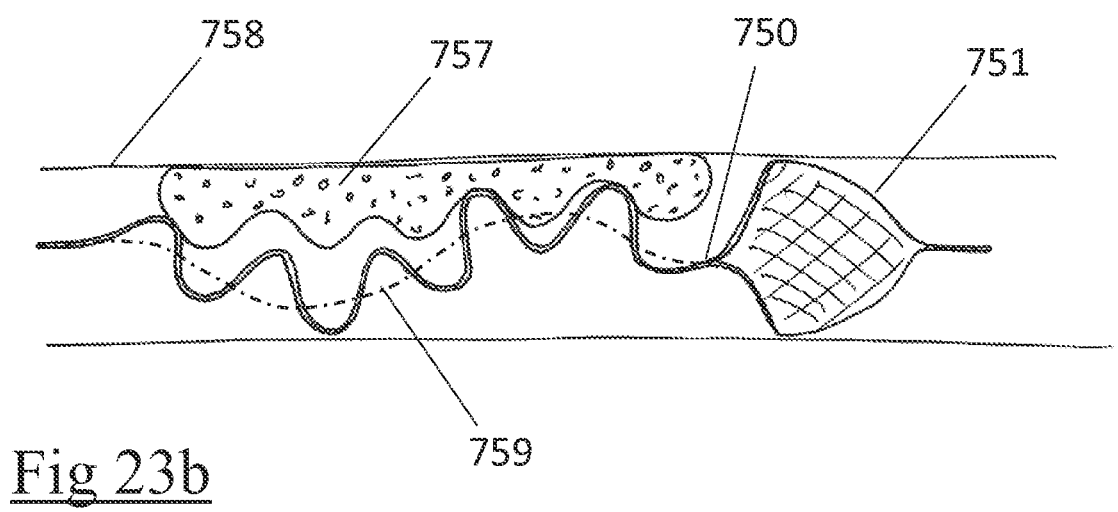

FIG. 23b shows the system of FIG. 23a when retraced into a larger diameter more proximal vessel segment 758. In this larger diameter vessel the body section 754 adopts a second wave pattern generally described by centerline 759. This may be achieved by configuring the device to adapt the shape shown in FIG. 23b in its freely expanded state, which may be done by heat setting a Nitinol device in this shape for example. Thus the device when collapsed within a microcatheter for delivery has a certain stored energy. Upon deployment within a clot a significant portion of this energy is released to enable the device to adopt the short wavelength pattern of FIG. 23a. Upon retraction of the device into a larger diameter vessel the remaining stored energy is exerted to enable the device to adopt a superimposed long wavelength pattern as shown in FIG. 23b, which helps the device retain a grip on the captured clot by increasing the effective diameter of the device and maintaining apposition with clot and the vessel wall.

Figure 24A:
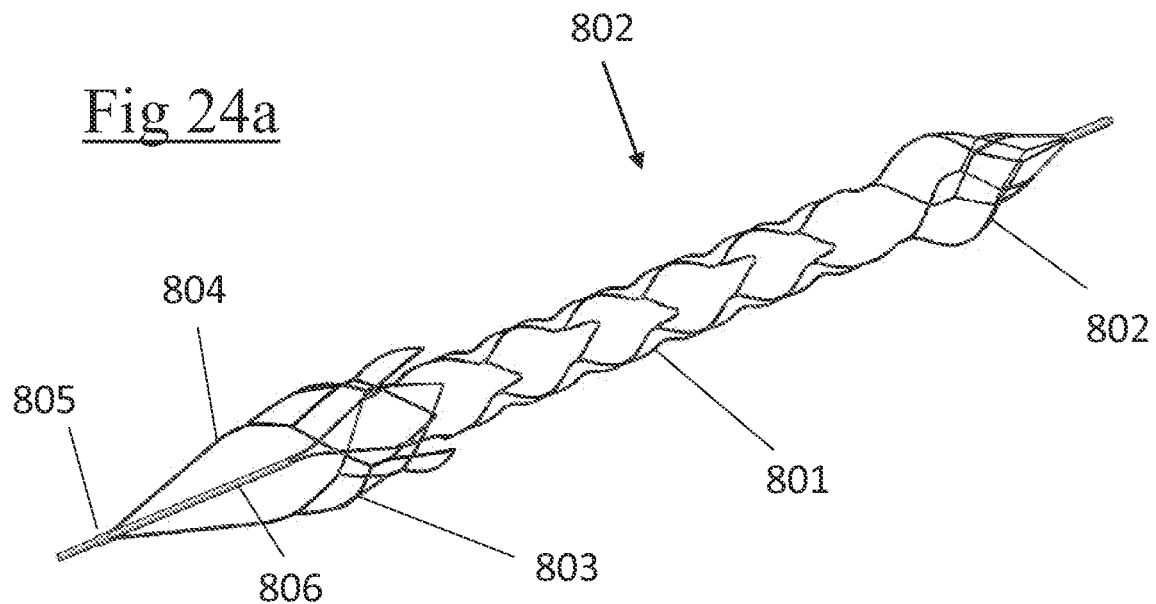
FIGS. 24a-24c are views of another clot retrieval device of the invention.

This and other embodiments of the device may have additional wave pattern features, such as the curvature of side rails 701 and 702 in plan view in FIG. 22b, and the "out of plane" protrusions of features such as floating crowns 705 which are illustrated more clearly in FIGS. 21b and 21c The device 800 shown in FIG. 24a is another embodiment of the invention. This device consists of a mid-section 801 which in one embodiment is formed from a flat sheet and set in a series of wave shapes with a flat or profiled cross section. This section can also be formed by flattening a cut tube or using an oval or elliptical cross sectional shape tube when viewed along the vessel axis. In the embodiment shown, the mid-section 801 is combined with a fragment protection feature 802 and a proximal section 803. The proximal section may be a separate component and be formed in a tubular or cone shape. This section is connected to the device by one or more proximal struts 804, which are connected to a collar 805 positioned on the device shaft 806.

Figure 24B:
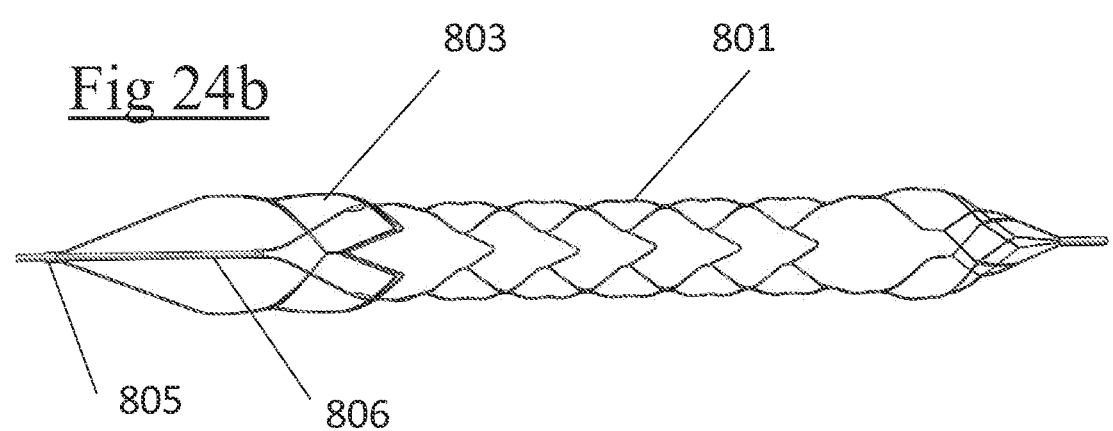
Figure 24C:
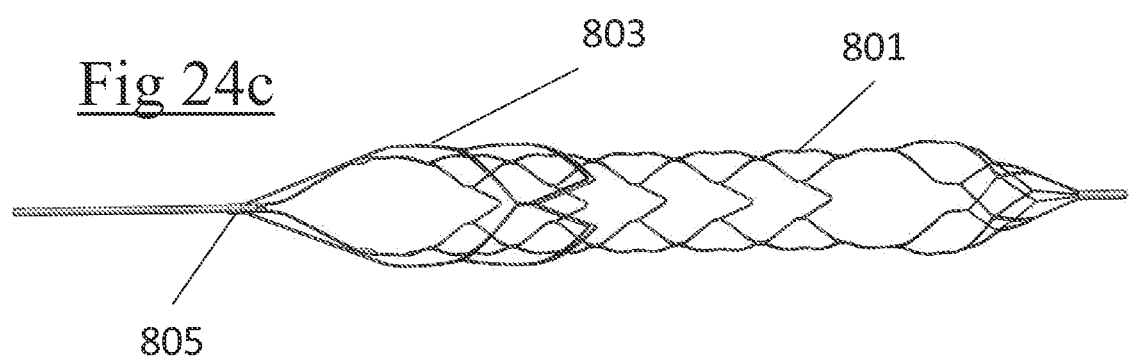

The collar 805 may be fixed to shaft 806 or it may be free moving and be able to slide along the shaft. FIG. 24b shows a plan view of the device with the proximal section 803 in a proximal position relative to the mid-section 801. This is typical of the orientation of the device on initial deployment in the blood clot or occlusion. When the device 800 is retracted to dislodge the clot, the proximal section 803 initially remains static due to friction between the component and the vessel wall. On device retraction the mid-section 801 and clot move proximally relative to section 803 allowing the clot to be partially retracted under the struts of the proximal section. This helps to grip the clot and prevent loss of contact with the clot as the device is retracted into larger diameter vessels. Continued retraction of the device causes all sections to move proximally as a single unit as travel of the proximal section 803 is limited by the collar 805 on shaft 806 contacting the proximal joint of the mid-section 801. The device and clot can then be retracted to a proximal catheter for removal from the vasculature.

Figure 25A:
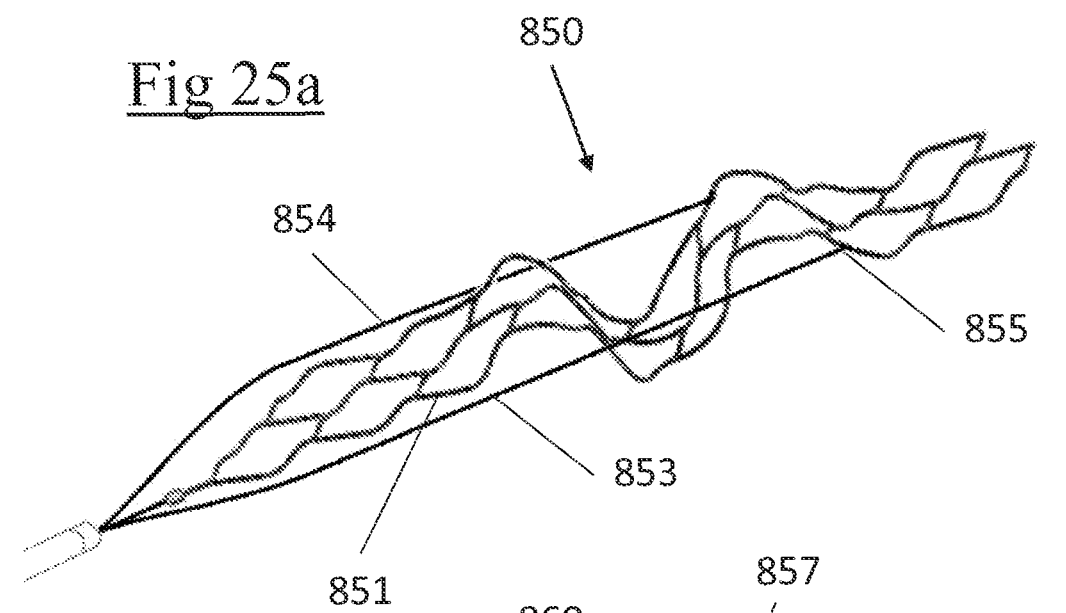
FIGS. 25a-25c are views of a further clot retrieval device of the invention.
Figure 25B:
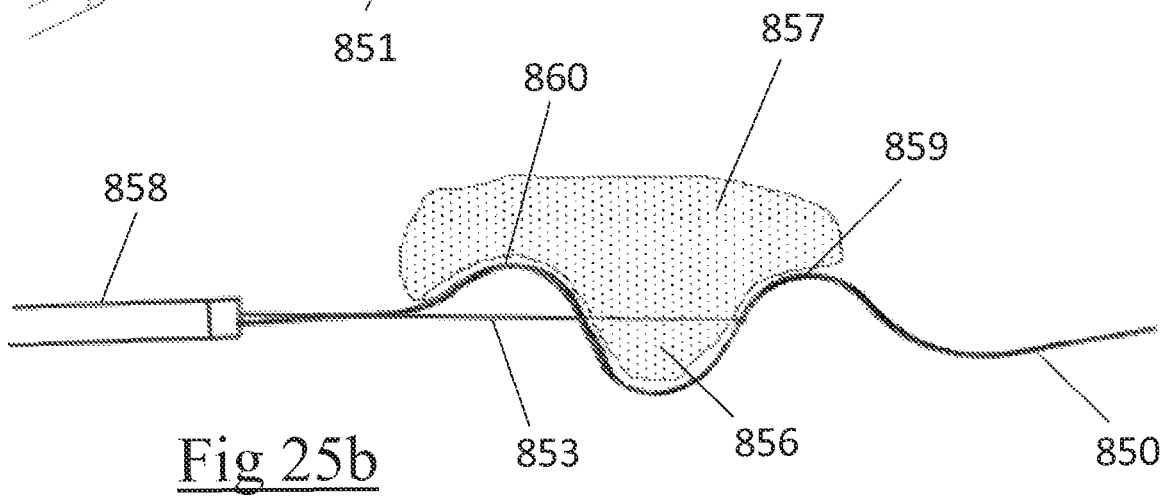

FIG. 25a shows an isometric view of another embodiment of the invention. In this device 850 the body section 851 is formed with a longitudinal wave shape similar to that described in FIG. 22. The body section 851 is also connected to two or more pull wires 853 and 854 at one or more connection points 855. These pull wires 853, 854 extend to a proximal handle (not shown) where the user or physician can apply tension to the wires. By placing these wires under tension the wave profile of the body section 851 can be modified and the pitch distance between peaks 859 and 860 can be shortened. This can cause increased pinching of the clot within the valley 856 sections of the wave shape. FIG. 25b shows the device 850 deployed in a vessel (not shown) and engaging with a blood clot 857. By actuating the pull wire 853 through the microcatheter 858, the clot 857 is gripped and compressed in the valley section 856 of the device.

Figure 25C:
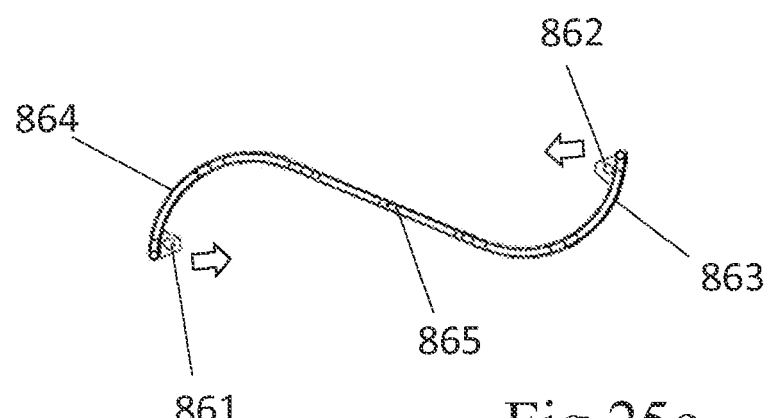

FIG. 25c shows an end view along the vessel axis of another iteration of the device. In this design, applying tension to the pull wires 861 and 862 by the user causes the side wings of the 'S' shape 863 and 864 to move in towards the diameter section 865 of the 'S'. When this device is deployed in contact with a blood clot (not shown), the actuation of the side wings 863 and 864 pinch the clot improving the grip of the device on the clot. Alternatively by pushing the wires 862 and 861 the user may improve the ability of the device to expand fully and engage the clot over a bigger area.

Figure 26A:
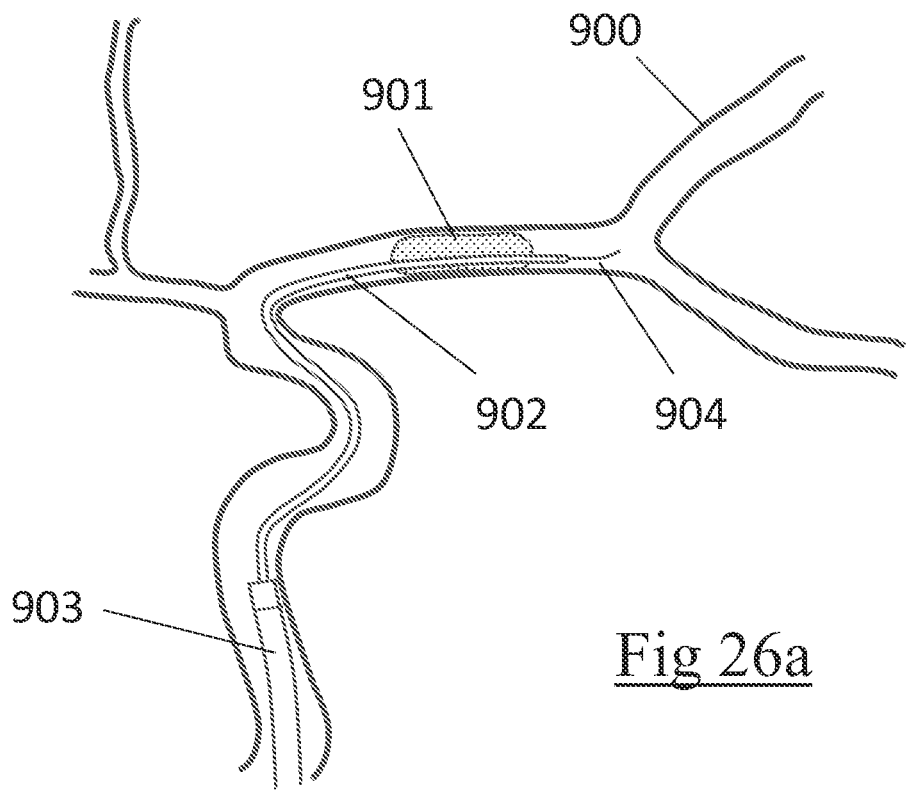
FIGS. 26a-26d illustrate a method of use of a clot retrieval device of the invention.
Figure 26B:
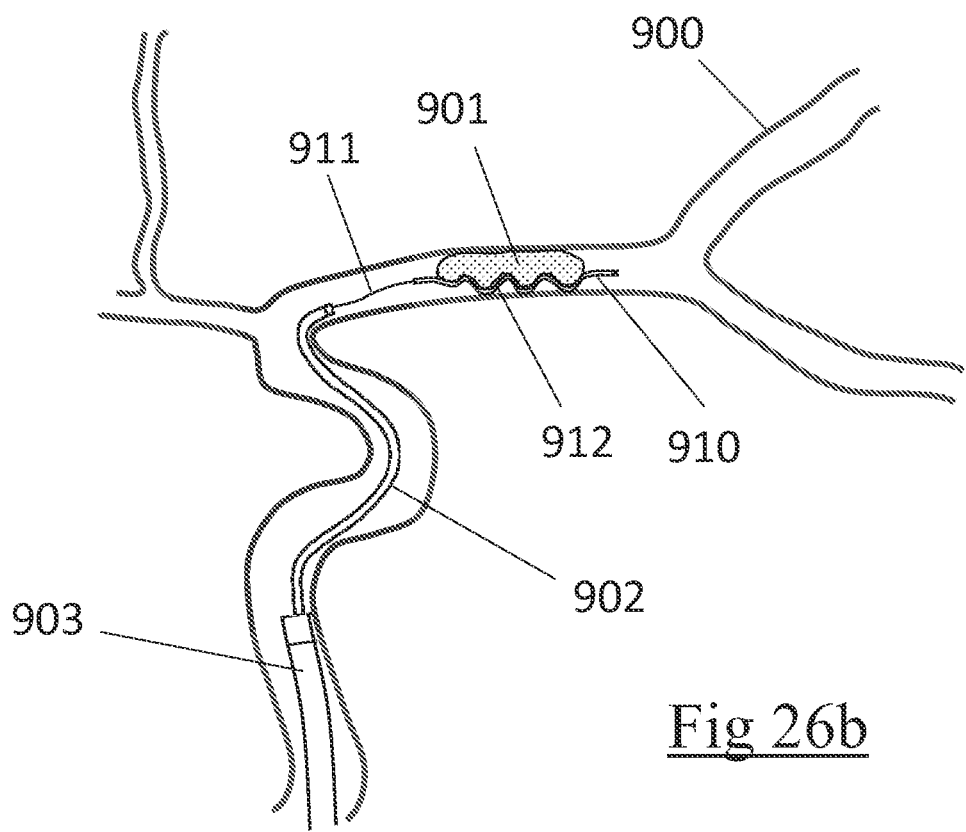
Figure 26C:
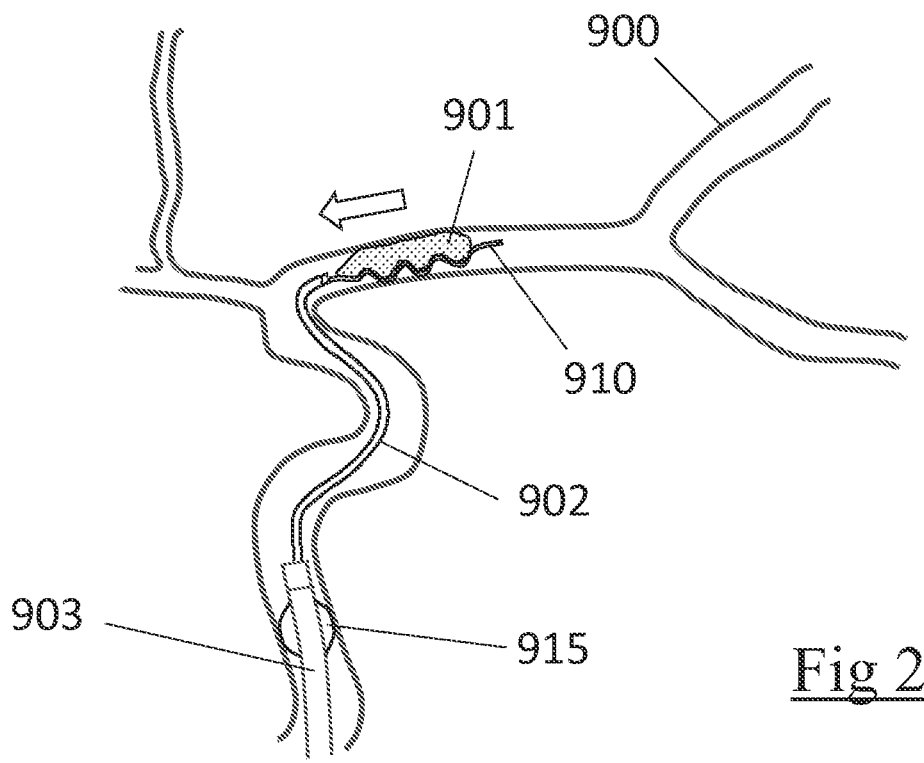
Figure 26D:
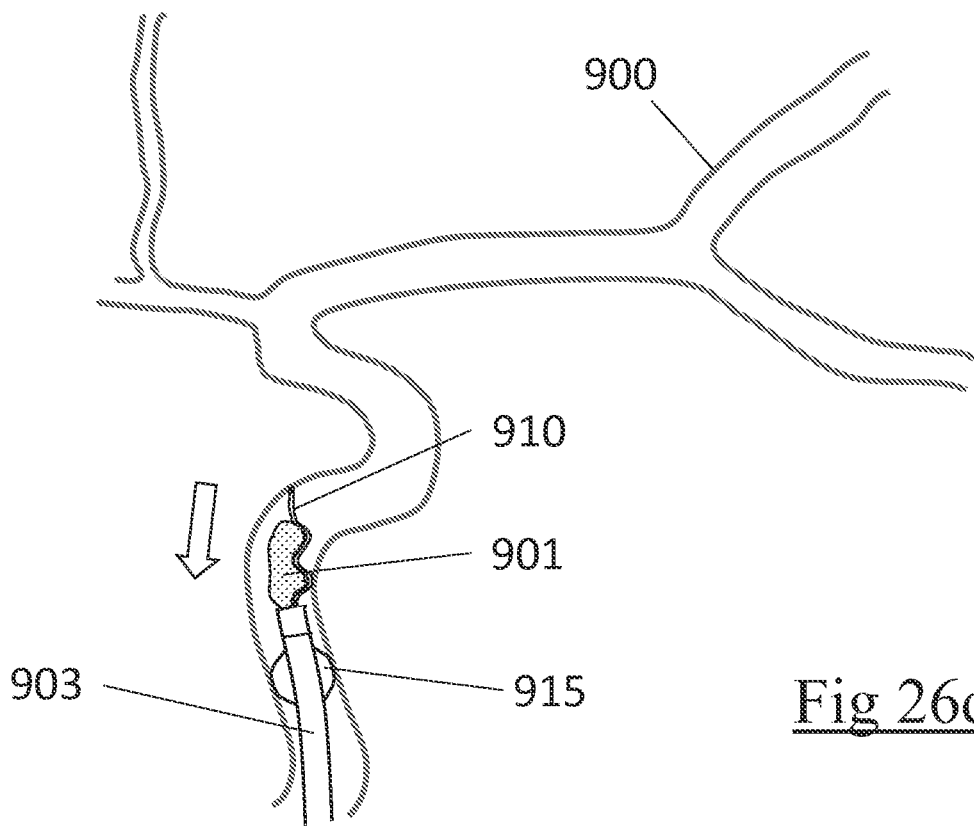

FIGS. 26a-26d show a method of use of a device of this invention. A guidewire 904 and microcatheter 902 are inserted in the vasculature 900 and are advanced across the obstructive clot 901 using conventionally known techniques. When the microcatheter 902 is positioned distal to the occlusive clot 901, the guidewire 904 is removed from the vasculature 900 to allow the clot retrieval device 910 to be advanced through the microcatheter 902. The device 910 is advanced in a collapsed configuration until the distal tip of the device reaches the distal end of the microcatheter 902. The microcatheter 902 is retracted while the position of device 910 is maintained to deploy the clot retrieval device across the clot 901 in a manner that the distal end of the device 910 is preferably positioned distal of the clot 901. The device 910 consists of a clot engagement portion 912 connected to an elongated proximal shaft portion 911. The device 910 expands so that it engages with the occlusive clot in a wave pattern which causes local compression of the clot in discrete regions adjacent the peaks of the device, but causes minimal overall compression on the bulk of the clot body. The device 910 may be allowed to incubate for a period of time within the clot 901 if desired. Flow arrest in the vessel may be utilised by inflating a balloon 915 on the guide catheter as per standard technique. Retracting the device 910 dislodges the clot from its position in the artery and further withdrawal of the device retrieves the clot 901 until it can be retrieved into the guide catheter 903 or introducer sheath. FIG. 26d illustrates the clot engaged with the device during retrieval into the guide catheter 903. Flow occlusion, aspiration and other standard techniques may be used during the clot retrieval process. The device 910 may be rinsed in saline and gently cleaned before reloading in the insertion tool. The device 910 may be reintroduced into the microcatheter to be redeployed in additional segments of occlusive clot, if required.

FIGS. 27a-27d show schematic details of the device shown in FIGS. 26a-26d and illustrate one embodiment of the device shown in FIG. 23. FIG. 27a shows a side view of the device containing a clot engagement portion 930 and a proximal shaft 931. FIG. 27b shows a plan view of the device while FIG. 27d shows an isometric view of the same device. FIG. 27c shows the cross sectional view A-A as detailed in FIG. 27a. The device may be formed from a flat sheet and heat-set in a series of wave shapes while maintaining a flat cross section. In another embodiment the device may have a curved or profiled cross section or be formed by flattening a cut tube or using an oval or elliptical cross sectional shape tube when viewed along the vessel axis. As with all the embodiments shown, this device can incorporate a fragment protection feature, for example such as that illustrated in FIGS. 23a and 23b.

In one embodiment the amplitude of the wave pattern in the freely expanded state is between 0.5 and 3.0 times the diameter of the vessel in which the occlusive clot to be retrieved is situated. In a preferred embodiment the amplitude of the wave pattern in the freely expanded state is between 0.5 and 2.0 times the diameter of the vessel in which the occlusive clot to be retrieved is situated. In a most preferred embodiment the amplitude of the wave pattern in the freely expanded state is between 0.5 and 1.5 times the diameter of the vessel in which the occlusive clot to be retrieved is situated. The pitch of the wave pattern in the freely expanded state is preferably between 1.0 and 4.0 times the diameter of the vessel in which the occlusive clot to be retrieved is situated. The pitch of the wave pattern in the freely expanded state is preferably between 0.5 and 2.0 times the amplitude of the wave pattern. In a preferred embodiment for use in a human middle cerebral artery the amplitude of the wave pattern is between 2.0 mm and 6.0 mm and the pitch of the wave pattern is between 3.0 mm and 8.0 mm.

Figure 28A:
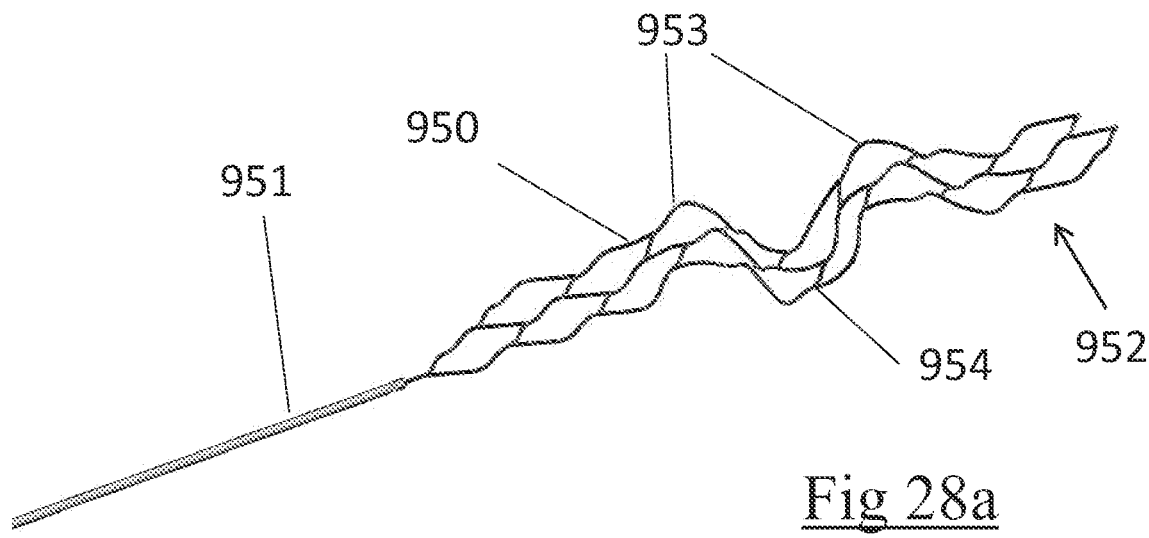
FIGS. 28a-28c are an isometric, side and plan views of a clot retrieval device.
Figure 28B:
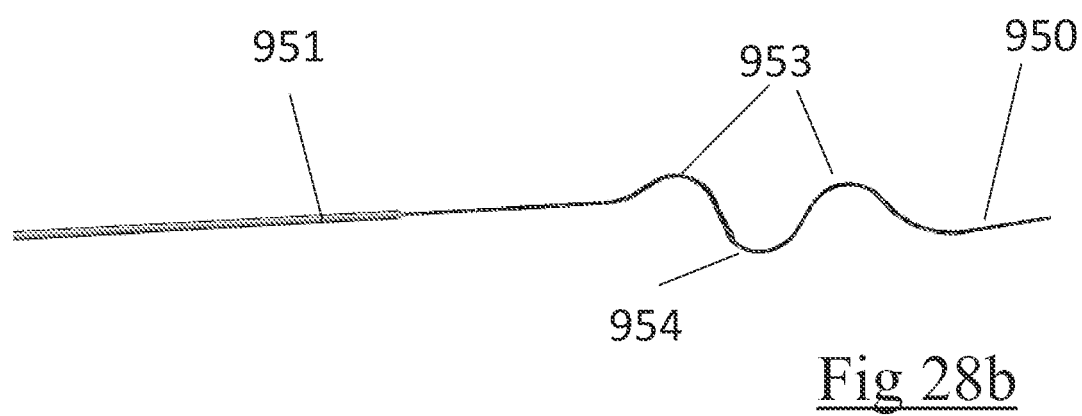
Figure 28C:
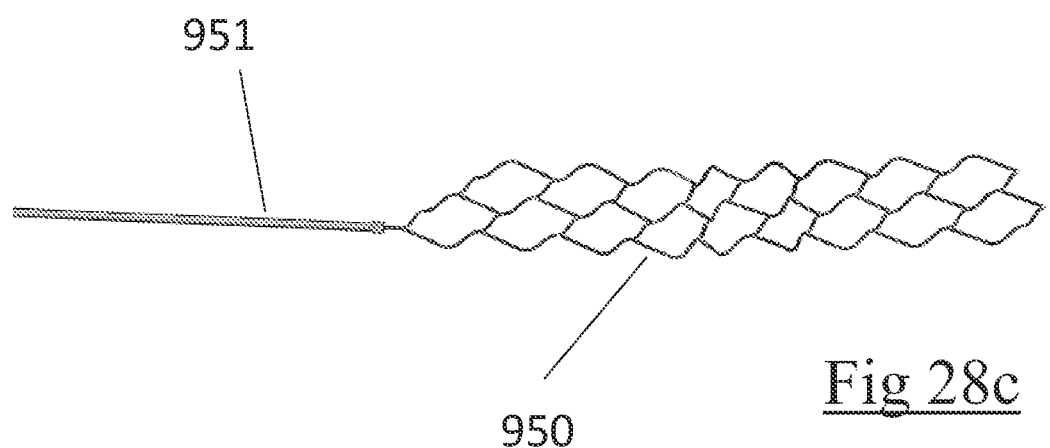

Another embodiment of the device is shown in FIGS. 28a-28c. An isometric view of the device is shown in FIG. 28a, while FIG. 28b shows a side view and FIG. 28c shows a plan view of the same device. The device 952 consists of a clot engagement section 950 connected to an elongated shaft 951. Section 950 may be formed by laser cutting a cell pattern into a flat sheet and heat setting into a partial or full wave pattern to engage with the clot to provide good dislodgement grip but minimal gross clot compression. Such a device may comprise any of the cell patterns disclosed elsewhere herein, and may be used to retrieve clot as described in relation to FIGS. 26a-d. The wave-like shape of the device varies the contact pressure between the clot and the device along the length of the device, creating peaks 953 in which the device exerts a relatively high compressive force on the clot and troughs 954 in which the device exerts little or no compressive force on the clot. The troughs 954 between the peaks 953 serve as a reception space into which the clot can freely flow as it compressed at peaks 953. The regions of higher compression allow the struts of the device to embed within the clot, creating a mechanical grip at both a microscopic (strut) and macroscopic (device wave pattern) level. The device can also elongate when placed under tension such as during the dislodgement of a clot from the vasculature. This minimizes the linear compression of the clot and may elongate the clot during dislodgement reducing the friction between the clot and the vessel wall and hence the dislodgement force required by the device to remove the clot.

Figure 29A:
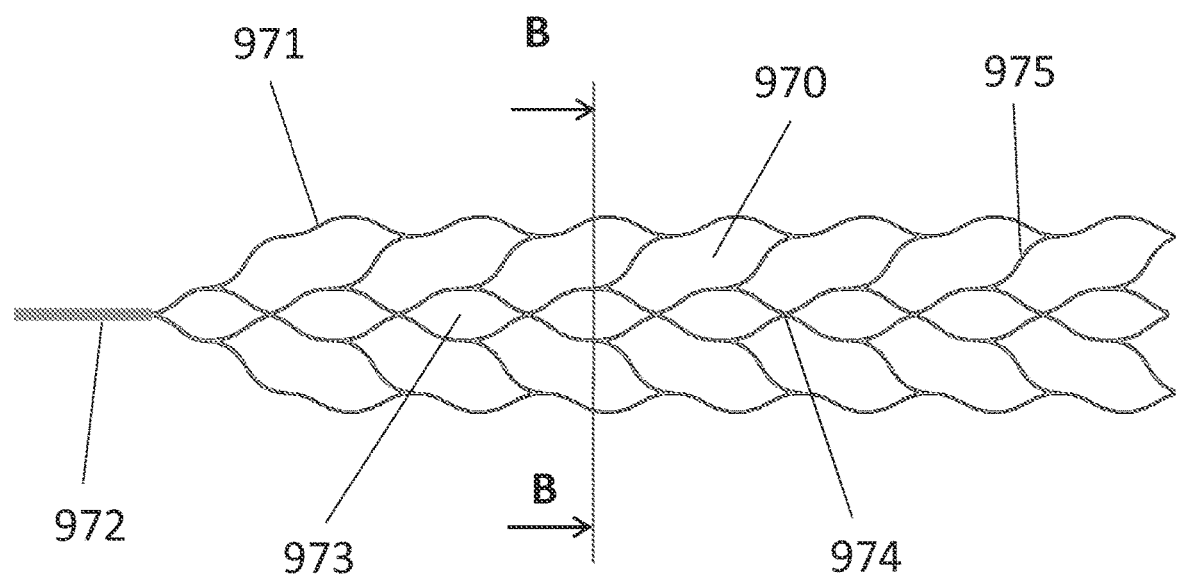
FIGS. 29a and 29b are plan and section views of another clot retrieval device of the invention.

FIG. 29a shows an example of a different flat device pattern that may be formed into a longitudinal or lateral wave-like shape. The cut pattern may be optimized to align particular cell features such as crowns or cross struts with the peaks and troughs of the wave pattern to maximize clot embedding and grip. For example the row of cells 973 may be aligned with the wavelength so that the crowns 974 are positioned at the peak or trough (maximum or minimum wave amplitude) of the device wave. Similarly cross struts 975 may be positioned to be at the peak or trough of the wave, or at the centerline mid wave height. The outer edge of the device 971 may be curved to minimize vessel contact pressure.

Figure 29B:
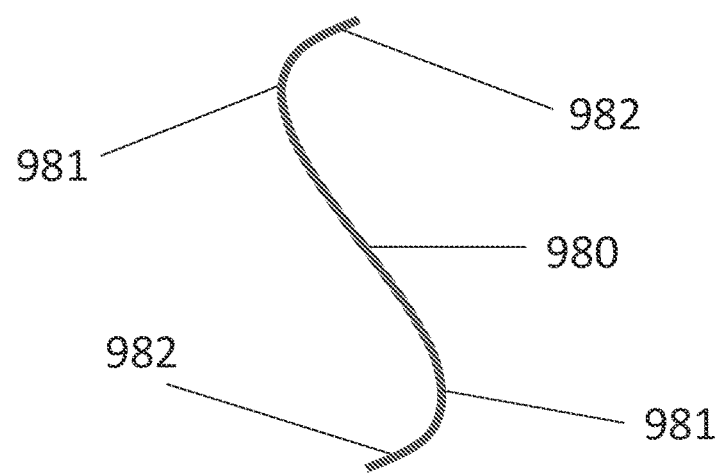

The device illustrated in FIG. 29a may have a flat, curved or profiled cross section when viewed along the vessel axis, for example FIG. 29b shows a cross sectional view (B-B) of this embodiment. This cross sectional view illustrates a curved profile which can be heat set into the device prior to or as part of the forming process to produce the wave pattern. The cross sectional shape of the device may be a combination of flat and curved sections as shown in FIG. 29b, where the device is flat in the mid-section 980 combined with a curve section each side 981 and an additional straight section 982.

Figure 30A:
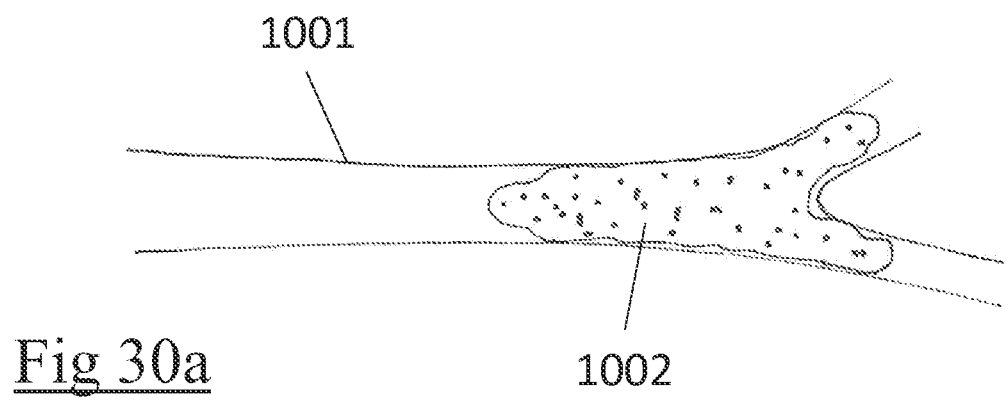
FIGS. 30a-30f illustrate a method of use of another clot retrieval device of the invention.
Figure 30B:
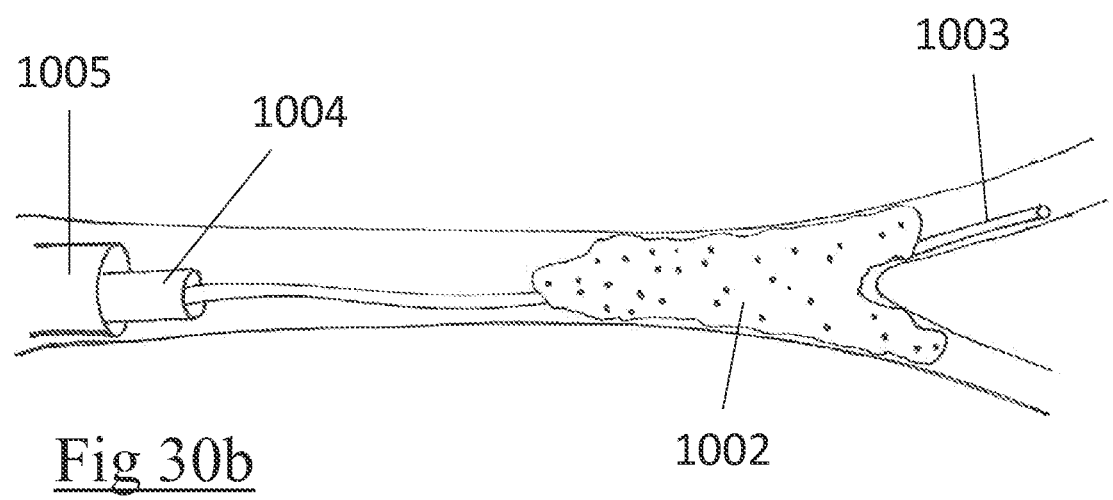
Figure 30C:
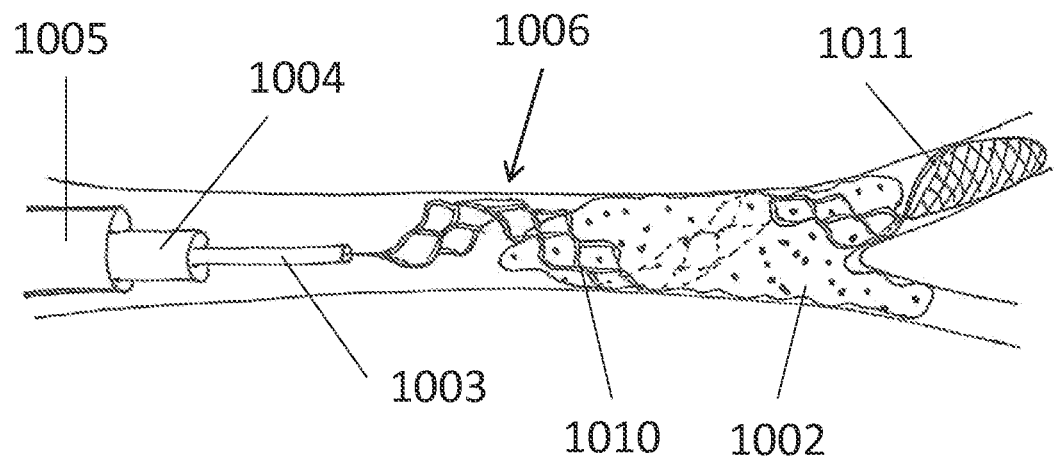
Figure 30D:
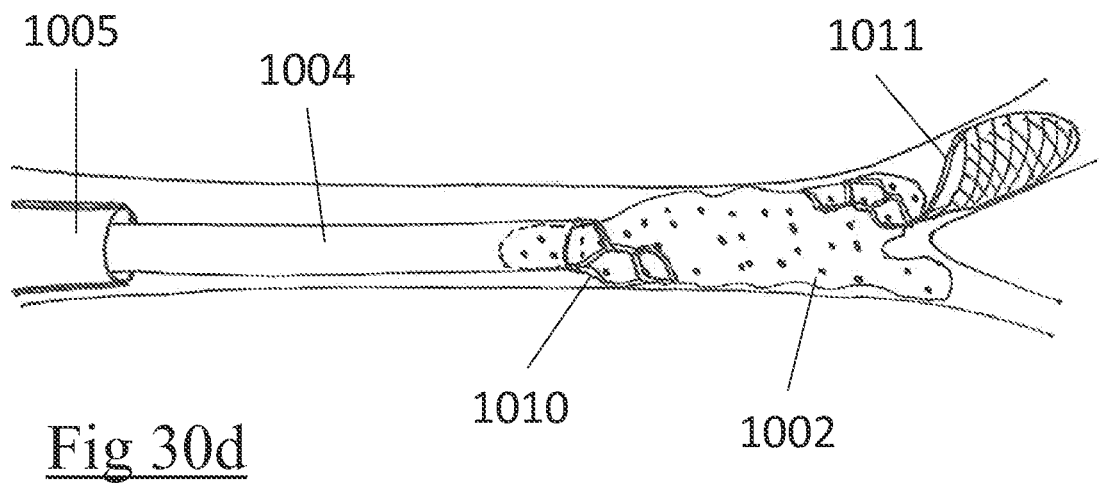

FIGS. 30a-30f show a method of use of another device 1006 of this invention, where the device adopts a generally spiral or helical configuration in the freely expanded state similar to that shown in FIG. 12. This device can be formed by laser cutting the required strut pattern from a tube or by cutting a flat sheet and then wrapping the flat part around a mandrel prior to heat-setting. FIGS. 30a-30f shows a method of use of a device of this invention. FIG. 30a shows a representation of an artery 1001 with a bifurcation and an occlusive clot 1002 positioned at the bifurcation. A microcatheter 1003 is inserted in the artery 1001 and is advanced across the obstructive clot 1002 using conventionally known techniques. The clot retrieval device 1006 can then be advanced through the microcatheter 1003 to the target location. The microcatheter is retracted while the position of device 1006 is maintained to deploy the clot retrieval device across the clot so that the fragment protection section of the device 1011 is preferably positioned distal of the clot 1002.

Figure 30E:
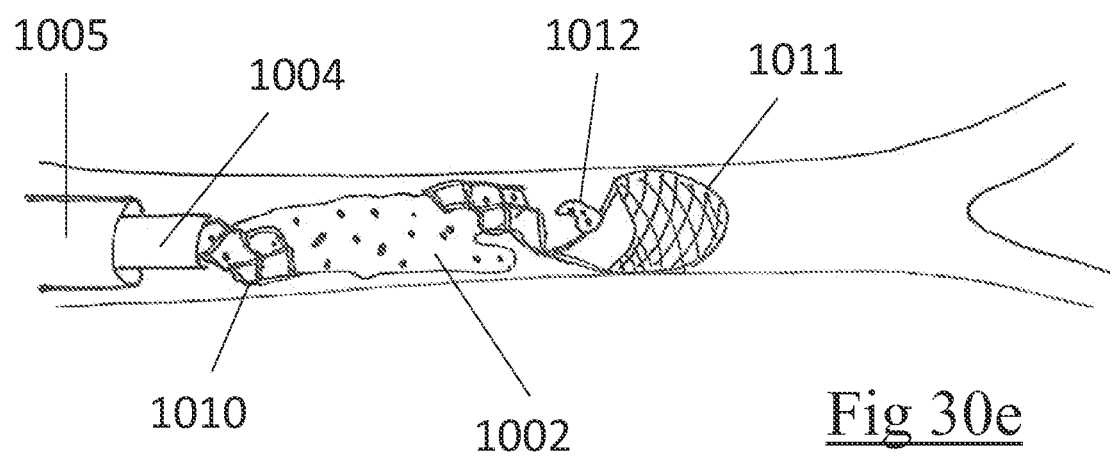
Figure 30F:
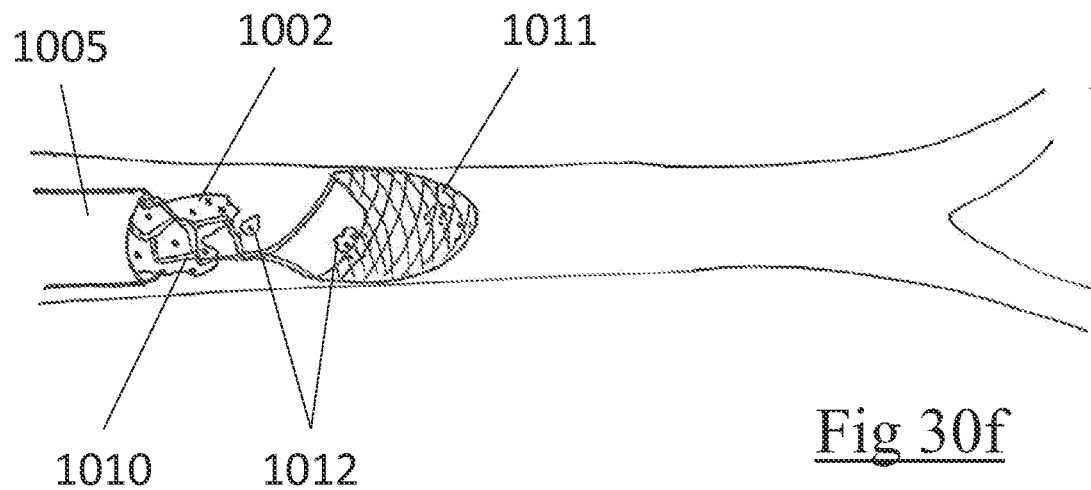

The device 1006 consists of a clot engagement portion 1010 connected to an elongated proximal shaft portion and a distal fragment protection section 1011. The clot engagement portion of the device 1010 expands into a helical configuration allowing the clot to partially or fully be enveloped by the device. This allows the device to grip and dislodge the clot while minimizing the overall compression of the clot body, making the clot easier to remove. On initial dislodgement the clot may be partially outside or proximal to the device and may migrate towards the center of the device during retraction to the guide catheter or sheath. The guide catheter 1005 and intermediate catheter 1004 are shown in FIGS. 30b-30f. In the method of use shown in FIG. 30d, the intermediate catheter 1004 is forwarded to the face of the clot 1002 and local aspiration applied prior to retrieval of the device and clot into the guide catheter 1005. This device can also be used with flow occlusion, aspiration and other standard techniques typically used during the clot retrieval process. FIGS. 30e-30f illustrate how the fragment protection portion of the device 1011 can capture fragments 1012 of the occlusive clot 1002 which can break off or be liberated during dislodgement and retrieval into the guide catheter or sheath 1005.

Figure 31:
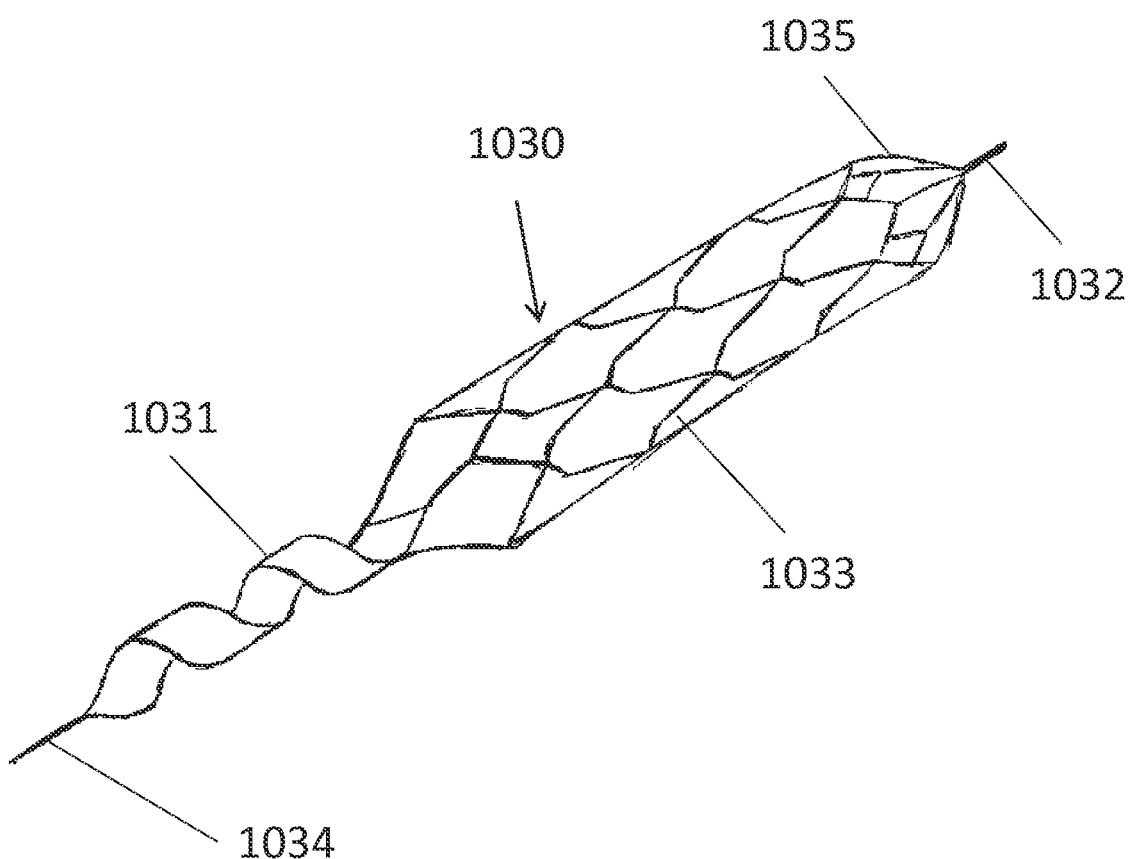
FIG. 31 is an isometric view of another clot retrieval device.

FIG. 31 shows another embodiment 1030 of the device where a proximal portion of the device is configured in a generally spiral or helical shape 1031 (similar to device 1006 of FIG. 30) and is connected to a radial or tubular portion 1033. The helical portion may be connected to a proximal shaft 1034 or additional portions of the device. The distal tubular portion contains a fragment protection section 1035 and is connected to a distal atraumatic radiopaque tip 1032. The helical section 1031 shown is a schematic representation and would typically consist of a laser cut cell pattern. The helical portion of the device 1031 is intended to provide improved performance for the dislodgement of fibrin rich sticky clots while the tubular section 1030 provides good clot retention during retraction to the guide catheter or sheath. As with all embodiments shown, the device may be rinsed and gently cleaned before reloading in the insertion tool. The device may be reintroduced into the microcatheter to be redeployed in additional segments of occlusive clot, if required.

Figure 32A:
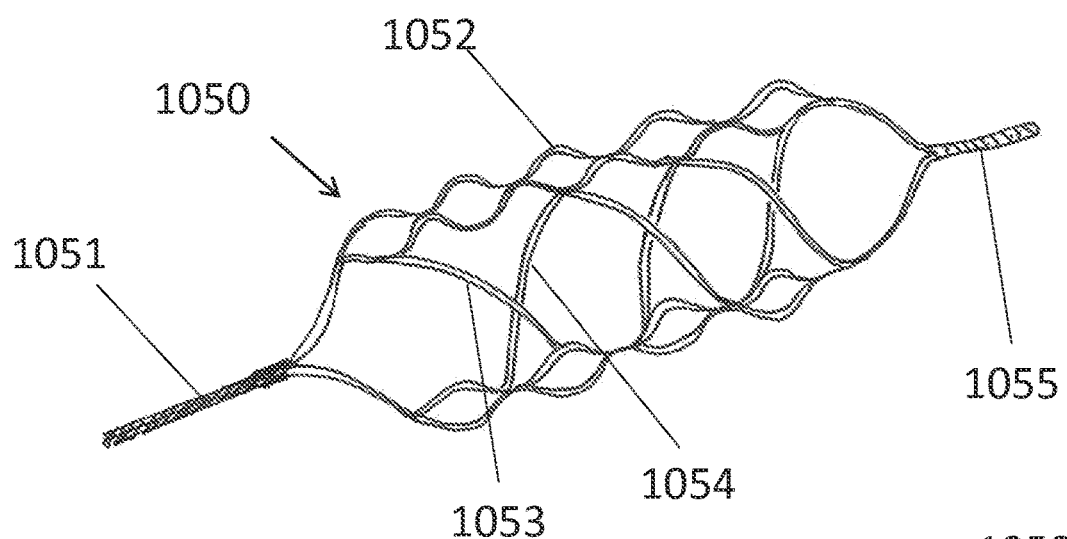
FIGS. 32a and 32b are an isometric view and an end view respectively of another clot retrieval device of the invention.
Figure 32B:
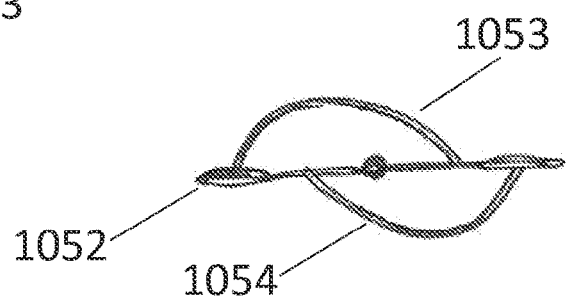

FIG. 32a shows an isometric view of another clot retrieval device of the invention comprising a clot engaging portion 1050 attached proximally to an elongate shaft 1051 and distally to an optional distal tip 1055. Clot engaging portion 1050 comprises a pair of side rails formed from cell elements 1052 to which are connected a plurality of clot engaging strut elements 1053 and 1054. Strut element 1053 and 1054 protrude from opposite sides of the plane defined by the side rails, as shown in end view FIG. 32b. This design is intended to operate in a similar principle to the previously disclosed wave-like devices, in that it is intended to provide local regions of high embedding force into the clot at cross struts 1053 and 1054, and adjacent regions of little or no embedding or radial force. The high embedding force at the cross struts creates a mechanical interference between clot and device, enabling the device to grip the clot securely, but because this embedding and resultant compression of the clot is applied over a very discrete and limited area there is minimal impact on the properties of the gross body of the clot. This is a very important advantage because the inventors have discovered that compression of the clot can cause the clot to become firmer and can increase its coefficient of friction, both of which can make it more difficult to retrieve.

Figure 33A:
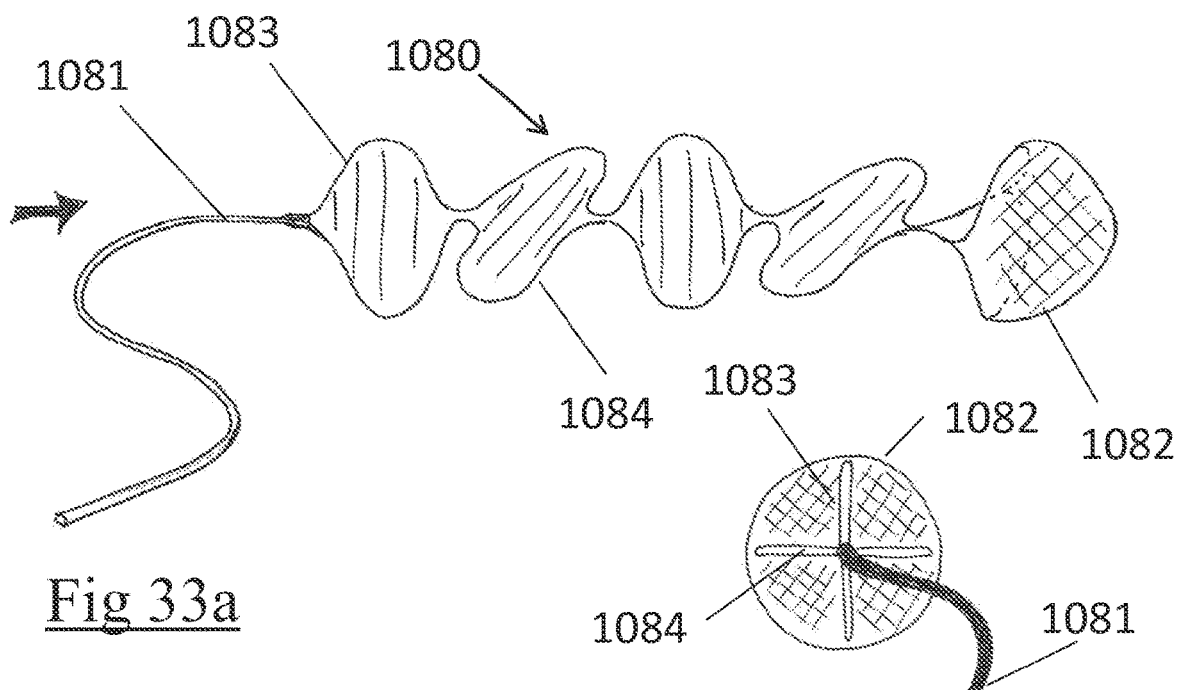
FIGS. 33a and 33b are an isometric view and an end view respectively of another clot retrieval device of the invention.
Figure 33B:
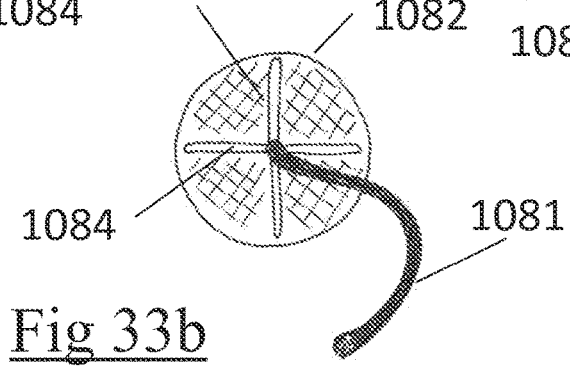

FIG. 33a shows an isometric view of another clot retrieval device of the invention comprising a clot engaging portion 1080 attached proximally to an elongate shaft 1081 and distally to an optional distal basket 1082. Clot engaging portion 1080 comprises a plurality of adjacent segments 1083 and 1084 which are aligned at approximately right angles to each other. Each segment 1083 or 1084 may be generally flat in shape, but the resultant overall structure 1080 has a three dimensional structure as can be seen in the end view shown in FIG. 33b. These alternating segments create a similar pattern of regions of high compression and regions of low compression in the clot to the previously shown wave-like designs, with similar advantages in terms of clot grip and retrieval with minimal force.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

What is claimed is:

1. A clot retrieval device for removing an occlusive clot from a blood vessel, comprising:
   a clot engagement section having a constrained delivery configuration and an expanded deployed configuration, wherein in the expanded deployed configuration, the clot engagement section has a cross-sectional shape along a longitudinal axis of the device of a sinusoidal wave-like form, and comprises:
      a plurality of peak sections formed by a plurality of cells and configured to vary contact pressure between the clot and the device along a length of the device; and
      a plurality of troughs formed by a plurality of cells and located between respective peak sections, the plurality of troughs comprising a clot reception space;
   wherein each peak is configured to exert a relatively high compressive force on the clot whereas each trough is configured to exert little or no compressive force on the clot, and
   wherein in the expanded deployed configuration, the peak sections are laterally spaced-apart and when being withdrawn into a catheter, are configured to pinch the occlusive clot from the blood vessel between the peak sections in the clot engaging section.

2. The device of claim 1, wherein the clot engaging section further comprises a pair of side rails formed from cells to which a plurality of clot engaging strut elements are connected, the cells protruding from opposite sides of a plane defined by the side rails.

3. The device of claim 1, wherein a wave pattern of the wave-like form has an amplitude of from 2.0 mm to 6.0 mm.

4. The device of claim 1, wherein a wave pattern of the wave-like form has a pitch of from 3.0 mm to 8.0 mm.

5. The device of claim 1, wherein in the expanded deployed configuration, the clot engagement section comprises the sinusoidal wave-like form of generally s-shape.

6. The device of claim 1, wherein the clot engagement section comprises a plurality of segments, adjacent segments being aligned at approximately 90° to each other.

7. The device of claim 1, the clot engagement section comprises a mesh of closed cells.

8. The device of claim 7, wherein the closed cells are diamond shaped.

9. The device of claim 1, wherein the device is substantially non-tubular.

10. The device of claim 1, wherein the clot engagement section comprises a plurality of patterns, including a first pattern comprising a wavelength and an amplitude and a second pattern comprising a wavelength and an amplitude larger than those of the first pattern.

11. The device of claim 1, comprising an activator for modifying a wave shape of the device.

12. The device of claim 11, wherein the activator comprises at least one push wire and/or at least one pull wire.

13. The device of claim 1, wherein, in the constrained configuration, the clot engagement section is substantially flat.

14. The device of claim 1, wherein the engagement section comprises two surfaces which face in generally opposite directions and one or both surfaces is engageable with the clot in the expanded deployed configuration.

15. A clot retrieval device for removing an occlusive clot from a blood vessel, comprising:
   a shaft;
   a clot engagement section connected to a distal end of the shaft and having a constrained delivery configuration and an expanded deployed configuration, wherein in the expanded deployed configuration the clot engagement section has a cross-sectional shape along a longitudinal axis of the device of a sinusoidal wave-like form, and comprises:
      a plurality of peak sections formed by a plurality of cells and configured to vary contact pressure between the clot and the device along a length of the device; and
      a plurality of troughs formed by a plurality of cells and located between respective peak sections, the plurality of troughs comprising a clot reception space; and a proximal section movable relative to the clot engagement section, wherein each peak is configured to exert a relatively high compressive force on the clot whereas each trough is configured to exert little or no compressive force on the clot, and wherein in the expanded deployed configuration, the peak sections are laterally spaced-apart and when being withdrawn into the shaft, are configured to pinch the occlusive clot from the blood vessel between the peak sections in the clot engaging section.

16. The device of claim 15, wherein the proximal section comprises a collar and proximal struts extending from the collar slidably movable relative to the shaft.

17. The device of claim 15, wherein at least some of the struts of the proximal section extend in a distal direction for at least partial capture of clot between the clot engaging section and the proximal struts on proximal movement of the collar relative to the proximal shaft.

18. A method from removing an occlusive clot from a blood vessel, comprising:

delivering a clot retrieval device to the occlusive clot in the blood vessel, the device comprising a clot engagement section having a constrained delivery configuration and an expanded deployed configuration, wherein in the expanded deployed configuration, the clot engagement section has a cross-sectional shape along a longitudinal axis of the device of a sinusoidal wave-like form, and comprises:

a plurality of peak sections formed by a plurality of cells and configured to vary contact pressure between the clot and the device along a length of the device; and a plurality of troughs formed by a plurality of cells and located between respective peak sections, the plurality of troughs comprising a clot reception space;

wherein each peak is configured to exert a relatively high compressive force on the clot whereas each trough is configured to exert little or no compressive force on the clot;

deploying the device to the expanded deployed configuration thereby causing the troughs of the device to embed with the clot;

exerting a relatively high compressive force, by the peaks, on the clot while exerting little or no compressive force, by the troughs, on the clot; and retrieving at least a portion of the device and the captured clot into a retrieval catheter, wherein in the expanded deployed configuration, the peak sections are laterally spaced-apart and when being withdrawn into the retrieval catheter, are configured to pinch the occlusive clot from the blood vessel between the peak sections in the clot engaging section.

19. The method of claim 18 further comprising: creating a mechanical grip between peaks of the device and the clot at regions of higher compression of the peaks.

20. The method of claim 18, further comprising minimizing linear compression of the clot during and/or elongating the clot during dislodgement by reducing the friction between the clot and the vessel wall by pinching the clot between peaks of the device.

* * * * *